(12) United States Patent
Hayashi et al.

(10) Patent No.: US 8,231,640 B2
(45) Date of Patent: Jul. 31, 2012

(54) SUTURE INSTRUMENT

(75) Inventors: Kensuke Hayashi, Yokohama (JP); Junji Shiono, Yokohama (JP)

(73) Assignee: Olympus Medical Systems Corp. (JP)

( * ) Notice: Subject to any disclaimer, the term of this patent is extended or adjusted under 35 U.S.C. 154(b) by 996 days.

(21) Appl. No.: 12/183,206

(22) Filed: Jul. 31, 2008

(65) Prior Publication Data
US 2010/0030237 A1 Feb. 4, 2010

(51) Int. Cl.
A61B 17/04 (2006.01)
(52) U.S. Cl. .......................... 606/144; 606/148; 606/139
(58) Field of Classification Search .................. 606/139, 606/142–148, 213, 232, 300, 99; 623/1.11; 600/104, 585
See application file for complete search history.

(56) References Cited

U.S. PATENT DOCUMENTS

| | | | |
|---|---|---|---|
| 6,066,146 A | 5/2000 | Carroll et al. | |
| 6,165,163 A * | 12/2000 | Chien et al. | 604/523 |
| 2003/0236535 A1 | 12/2003 | Onuki et al. | |
| 2004/0153074 A1* | 8/2004 | Bojarski et al. | 606/72 |
| 2007/0073320 A1 | 3/2007 | Mikkaichi et al. | |
| 2007/0073322 A1* | 3/2007 | Mikkaichi et al. | 606/153 |

FOREIGN PATENT DOCUMENTS

| | | |
|---|---|---|
| EP | 1 938 760 A1 | 7/2008 |
| JP | 2007-090062 | 4/2007 |
| WO | WO 2006/044837 A2 | 4/2006 |
| WO | WO2007/037326 | 4/2007 |
| WO | WO 2008/021969 | 2/2008 |

OTHER PUBLICATIONS

Search Report issued by European Patent Office in connection with corresponding application No. EP 09 00 9892 on Nov. 27, 2009.
Korean Office Action issued by the Korean Patent Office on May 11, 2011 in connection with corresponding Korean Patent Application No. 10-2009-69564.
English translation of Korean Office Action issued in connection with Korean Patent Application No. 10-2009-69564 on May 11, 2011.

* cited by examiner

Primary Examiner — Corrine M McDermott
Assistant Examiner — Mark Mashack
(74) Attorney, Agent, or Firm — Ostrolenk Faber LLP

(57) ABSTRACT

A suture instrument includes: a therapeutic insertion section having a suture section for suturing tissue; a cylindrical main operation unit; a rod section in the main operation unit, for discharging a suture thread and end section members connected to the suture thread; a pusher's distal end section for pressing the end section member; and a guide mechanism for rotating the rod section after linear movement of the pusher's distal end section at a position where one of the end section member is fed from a distal end of the suture section, the rod section being rotated in the circumferential direction to a position where the other one of the end section members is fed from the distal end of the suture section, so that each one of the end section members is discharged one after another and so that the end section members can be separated finally.

8 Claims, 21 Drawing Sheets

SUTURE INSTRUMENT

BACKGROUND OF THE INVENTION

1. Field of the Invention

The present invention relates to a suture instrument used to be inserted into a body cavity. To be more specific, the present invention relates to a suture instrument used to suture a hole etc. formed on a hollow organ, e.g., a stomach or a digestive organ by using a suture thread having anchors attached to the ends thereof.

2. Background Art

A conventionally known suture instrument uses a suture thread having anchors attached to the two ends thereof for the purpose of suturing a hole or a laceration formed on a hollow organ such as a stomach or a digestive organ (for example, see WO2007-37326). A suture instrument of this type sutures an organ by locking a tissue around the hole within or in the exterior of the tissue with anchors attached to the two ends of the suture thread, constricting the suture thread, and attracting the tissue having the anchors locked thereto.

In order to conduct a reliable suturing of tissues by using the suture instrument disclosed in WO2007-37326, the anchors loaded in the distal end of the suture instrument must be discharged from the distal end one after another reliably into opposed tissues with respect to the hole, and the tissues must be locked by the anchors. For this reason, an annular groove is formed on the surface of each anchor of the suture instrument disclosed by WO2007-37326 to engage with a projection provided on the inner surface of the needle disposed on the distal end of the suture instrument. In this configuration, a user can feel and acknowledge the discharge of the anchor based on the disengagement of the projection from the groove.

SUMMARY OF THE INVENTION

A first aspect of the present invention is a suture instrument which includes: a therapeutic insertion section having a suture section formed on the distal end thereof and suturing a tissue endoscopically; a cylindrical main operation unit connected to a proximal end of the therapeutic insertion section; a rod section inserted into the main operation unit along an axial line of the main operation unit from a proximal end of the main operation unit, the rod section conducting operations for discharging a suture thread and a plurality of end section members connected to at least an end of the suture thread from a distal end of the suture section; a pusher's distal end section for pressing the end section member to move corresponding to the operations conducted by the rod section; and a guide mechanism for guiding and discharging the plurality of the end section members one after another by halting a linear movement of the pusher's distal end section at a position where the pusher's distal end section has been moved linearly so that one of the end section members is discharged from the distal end of the suture section; allowing another one of the end section members to be prepared for discharge by providing a rotative movement to the rod section by a predetermined degree in a circumferential direction, and guiding the linear movement and the rotative movement repeatedly, wherein the guide mechanism includes: a cylindrical member disposed to the proximal end of the therapeutic insertion section and connected to the suture section via a connection member; an engagement member fixed to a distal end of the rod section and inserted into the cylindrical member; a guide groove having: a plurality of longitudinal grooves advancing in an axial line direction and formed on a side of one of the cylindrical member and the engagement member in the circumferential direction, each one of the plurality of longitudinal grooves being disposed by a different angle around the axial line and being capable of guiding the pusher's distal end section along the axial line freely-advancing and retractably; and a plurality of lateral grooves advancing to connect end sections of the plurality of longitudinal grooves with each other in the circumferential direction and to limit an advancing movement or a retracting movement of the pusher's distal end section; and a projection section fixed to the other one of the cylindrical member and the engagement member and engaging with the guide groove, and wherein a protrusion section provided in the guide groove limits movement of the projection section along the guide groove.

A second aspect of the present invention is a suture instrument which includes: a therapeutic insertion section having a suture section formed on the distal end thereof and suturing a tissue endoscopically; a cylindrical main operation unit connected to a proximal end of the therapeutic insertion section; a rod section inserted into the main operation unit along an axial line of the main operation unit from a proximal end of the main operation unit, the rod section conducting operations for discharging a suture thread and a plurality of end section members connected to at least an end of the suture thread from a distal end of the suture section; a pusher's distal end section for pressing the end section member to move corresponding to the operations conducted by the rod section; and a guide mechanism for guiding and discharging the plurality of the end section members one after another by halting a linear movement of the pusher's distal end section at a position where the pusher's distal end section has been moved linearly so that one of the end section members is discharged from the distal end of the suture section; allowing another one of the end section members to be prepared for discharge by providing a rotative movement to the rod section by a predetermined degree in a circumferential direction, and guiding the linear movement and the rotative movement repeatedly, wherein the guide mechanism further comprises a rotative cam mechanism for rotating the rod section in one way in the circumferential direction by a predetermined interval by pressing the rod section to move distally and for halting the rod section.

PREFERRED EMBODIMENTS

A suture instrument according to a first embodiment of the present invention will be explained as follows with reference to FIGS. 1 to 6.

Figure 1:
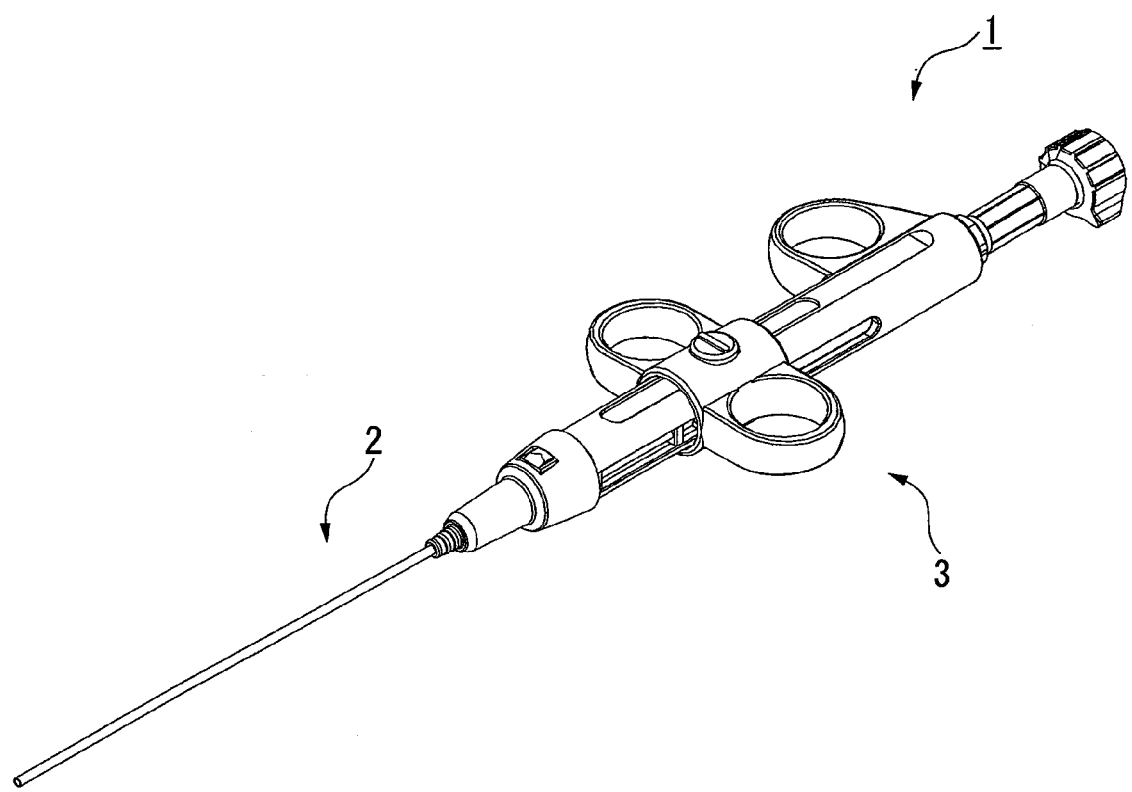
FIG. 1 shows a suture instrument according to a first embodiment of the present invention.

FIG. 1 shows a suture instrument 1 according to the present embodiment. The suture instrument 1 is configured to include: an elongated therapeutic insertion section 2 inserted into a body cavity; and an operation section 3, disposed proximally relative to the therapeutic insertion section 2, for operating each mechanism.

Figure 2:
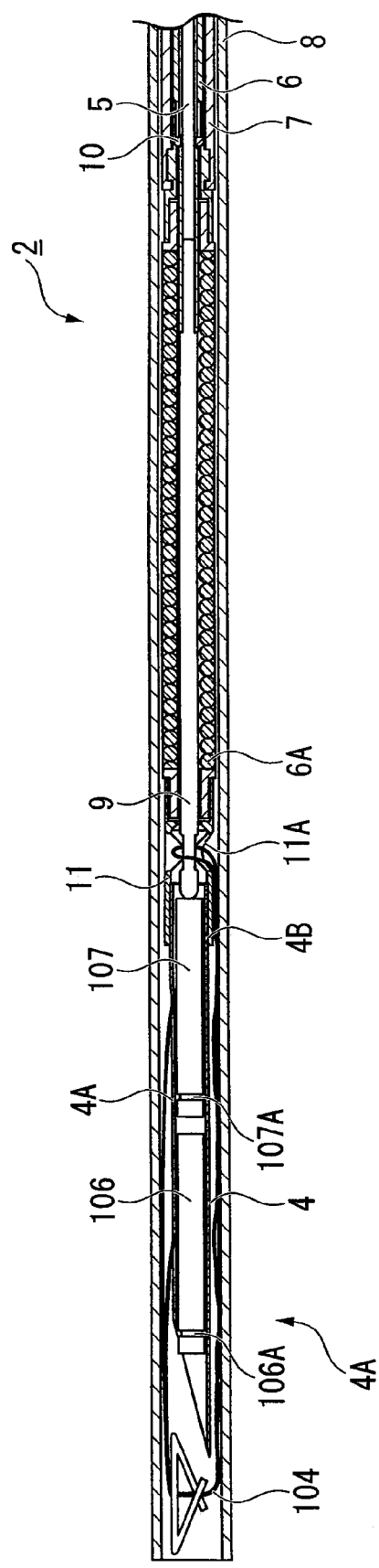
FIG. 2 is an enlarged fragmentary sectional view of the distal end section of the suture instrument.

FIG. 2 shows a part of a therapeutic insertion section 2 in an enlarged cross-sectional view. The therapeutic insertion section 2 is configured to include: a tubular outer sheath 8 which serves as an outer cylinder for the therapeutic insertion section 2; a needle 4, capable of advancing and retracting in an opening of the distal end, having a suture unit, which will be explained later, at the distal end thereof in the outer sheath 8; a pusher's distal end section 9 inserted into the proximal end of the needle 4 and being capable of advancing and retracting; a wire 5 for connecting the pusher's distal end section 9 to the operation section 3; a distal coil sheath 6A fixed to the proximal end section of the needle 4 and having the pusher's distal end section 9 and the wire 5 inserted therethrough; a tube 7 fixed to the proximal end of the distal coil sheath 6A and having the wire 5 inserted therethrough; and an inner coil sheath 6 disposed proximally relative to the distal coil sheath 6A and placed between the tube 7 and the wire 5 which is inserted into the inner coil sheath 6. The needle 4, the pusher's distal end section 9, and the distal end section of the outer sheath 8 form a suture section 2a for engaging a suture unit, which will be explained later, with a tissue and suturing the tissue.

The needle 4 is a hollow component made of metal or other materials having a groove 4A formed thereon. The needle 4 accommodates anchors (end section members) of the suture unit thereinside.

Figure 3:
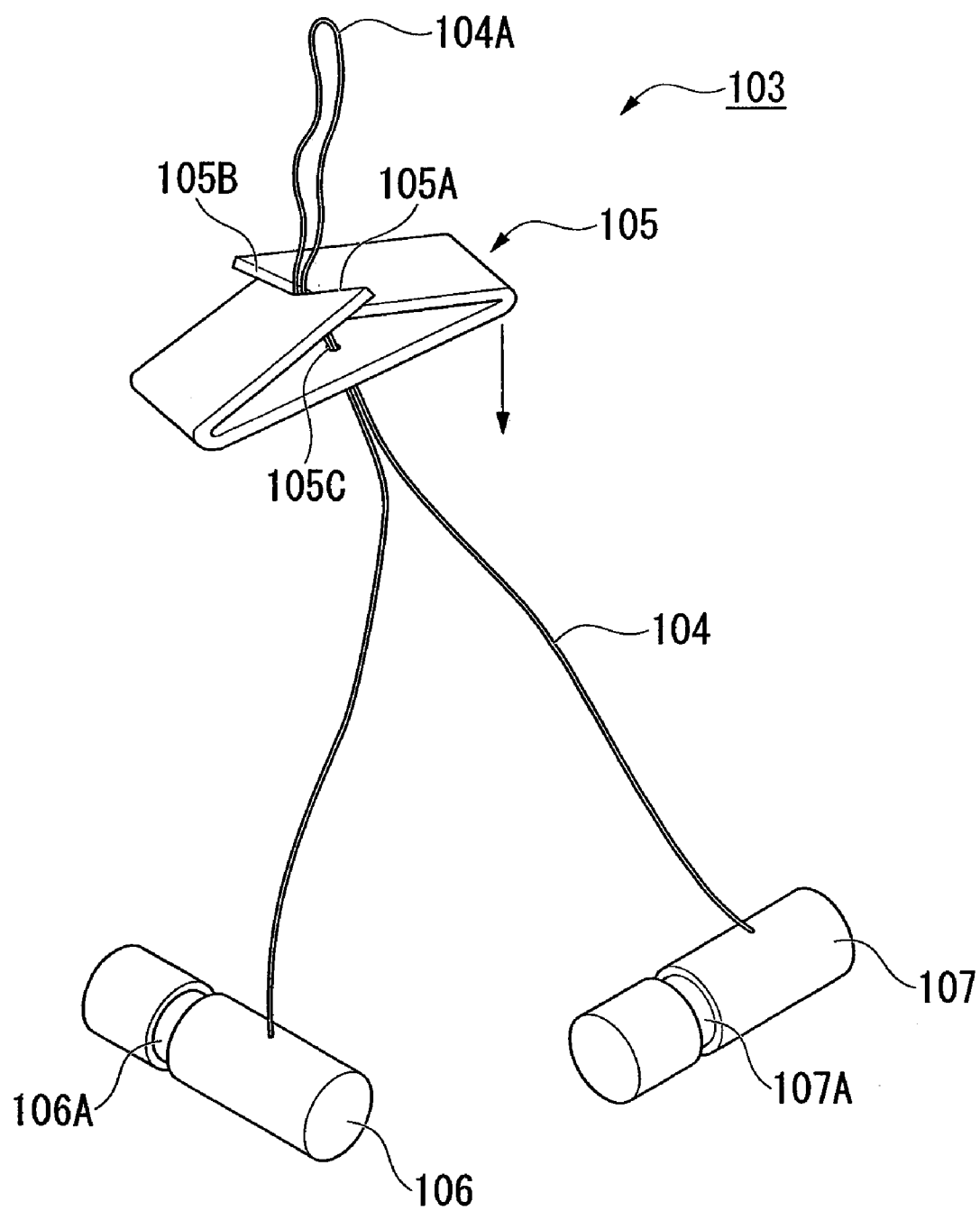
FIG. 3 shows a suture unit for used in the suture instrument.

FIG. 3 shows a suture unit 103 accommodated in the needle 4. The suture unit 103 is configured to include: a suture thread 104; a stopper 105 having the suture thread 104 passing therethrough; a bar-shaped first anchor 106 having a length L1 and attached to the two ends of the suture thread 104; and a bar-shaped second anchor 107 having the length L1.

The stopper 105 is formed so that end sections 105A and 105B disposed laterally in the longitudinal direction of, for example, a metal plate or a biodegradable resin plate are bent to oppose each other, and so that the end section 105A engages with the end section 105B.

The suture thread 104 hooked at a middle point 104A is inserted into a hole 105C provided in the vicinity of the center in the lateral direction of the stopper 105 from the surface opposite the end sections 105A and 105B so that the hooked suture thread 104 passes between the engaged end section 105A and the end section 105B. The movement of the stopper 105 during use thereof will be explained later.

As shown in FIG. 2, the first anchor 106 and the second anchor 107 of the suture unit 103 aligned in the axial line direction are accommodated in the needle 4 so that the first anchor 106 is disposed distally relative to the second anchor 107. The suture thread 104 connecting the anchor 106 to the anchor 107 is exposed to the exterior of the needle 4 from the groove 4A.

Also, the anchors 106 and 107 have engagement grooves 106A and 107A thereon respectively. The engagement grooves 106A and 107A each engaged with an engagement projection, which is not shown in the drawings, provided to project into the lumen of the needle 4 prevents an accidental discharge of each anchor 106 and 107 or a spontaneous falling thereof which may be caused by directing the distal end of the needle 4 downward perpendicularly.

The pusher's distal end section 9 formed by metal or other materials has a distal end inserted into the needle 4 from the proximal end 4B of the needle 4. Advancing the wire 5 in the axial line direction toward the distal end of the needle 4 causes the pusher's distal end section 9 to advance, thereby pressing the first anchor 106 and the second anchor 107 to allow them to be discharged thereoutside. The section of the pusher's distal end section 9 connected to the wire 5 forms an abutment section 10 which is a step section bulging from the outer periphery of the distal end of the wire 5 in a radial direction since the pusher's distal end section 9 has an outer diameter greater than the outer diameter of the wire 5.

While it is preferable to form the wire 5 by a single line of wire because a pressing force applied by using the operation section 3 can be transmitted to the pusher's distal end section 9, preferably, a multi-wire formed by stranded metal elemental wires, or a coil wire formed by winding metal elemental wires or a multi-wire spirally is applicable.

FIG. 2 further shows that the inner coil sheath 6 is a tubular coil sheath formed by winding the metal elemental wires or the multi-wire, and that the wire 5 capable of advancing and retracting in the axial line direction is inserted therein. The inner diameter of the inner coil sheath 6 is designed to be smaller than the outer diameter of the abutment section 10 of the wire 5 so that the abutment section 10 formed by a step between the pusher's distal end section 9 and the wire 5 makes contact with the distal end of the inner coil sheath 6. That is, a fixed state of the positional correlation between the wire 5 and the inner coil sheath 6 can be maintained in this configuration in which the abutment section 10 makes contact with the distal end of the inner coil sheath 6.

The tube 7 is a flexible tubular member made of resin or other materials. In view of material property, it is preferable that the tube 7 is made of a resin or other materials. having little elongation into the axial line direction. The tube 7 is connected to the distal coil sheath 6A via a coupling tube 7A attached to the distal end of the tube 7. The distal coil sheath 6A is a spiral and made of flexible material, such as metal or other materials. In addition, the distal coil sheath 6A is connected to the proximal end 4B of the needle 4 unitarily via a connection tube 11.

The abutment section 10 is capable of freely advancing or retracting in the coupling tube 7A along the axial line direction since the inner diameter of the coupling tube 7A in the axial line direction is configured to be greater than the outer diameter of the abutment section 10 of the wire 5. On the other hand, the inner coil sheath 6 is configured incapable of entering the coupling tube 7A since the inner diameter of the coupling tube 7A in the axial line direction is smaller than the outer diameter of the inner coil sheath 6.

In addition, a through-hole 11A penetrating into the lumen of the needle 4 is provided on the outer periphery of the connection tube 11 in the circumferential direction. The hooked middle point 104A of the suture thread 104 of the suture unit 103 inserted from the through-hole 11A into the lumen of the connection tube 11 is placed around the pusher's distal end section 9 inserted therein. In addition, the positional correlation between the pusher's distal end section 9 and the through-hole 11A is configured so that the abutment section 10 is positioned proximally relative to the through-hole 11A when the pusher's distal end section 9 moves distally relative to the needle 4. The outer diameter of the pusher's distal end section 9 is maintained in a range where the pusher's distal end section 9 makes contact with the suture thread 104.

The outer sheath 8 is a coil sheath having the same structure as that of the inner coil sheath 6. The tube 7 and the needle 4 connected to the tube 7 unitarily and being capable of advancing or retracting in the axial line direction are inserted into the outer sheath 8. In addition, as shown in FIG. 2, the needle 4 and the suture unit 103 attached to the needle 4 can be accommodated fully in an inner space thereof while the tube 7 is retracted proximally.

Figure 4:
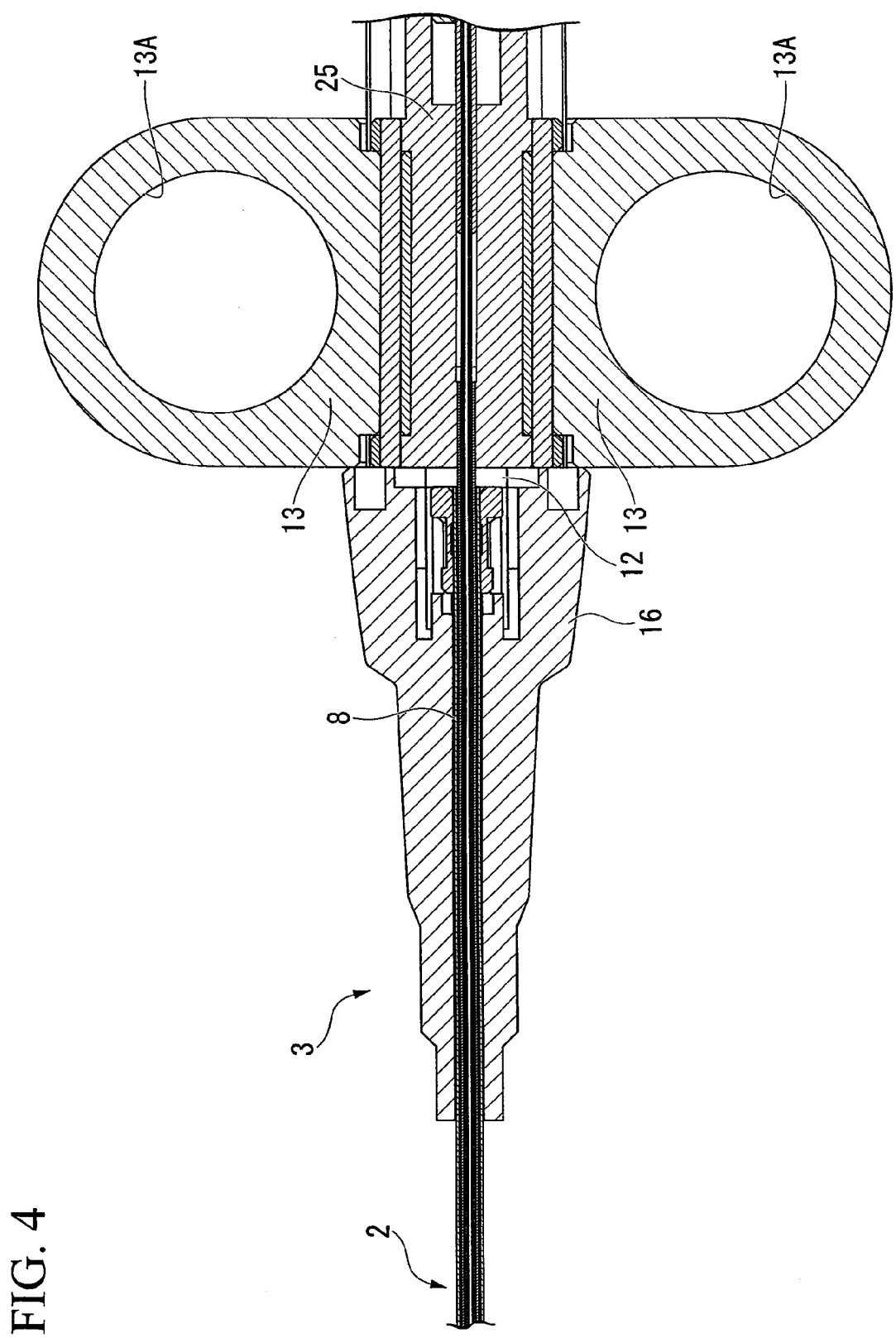
FIG. 4 is an enlarged fragmentary sectional view of an operation section of the suture instrument.
Figure 5:
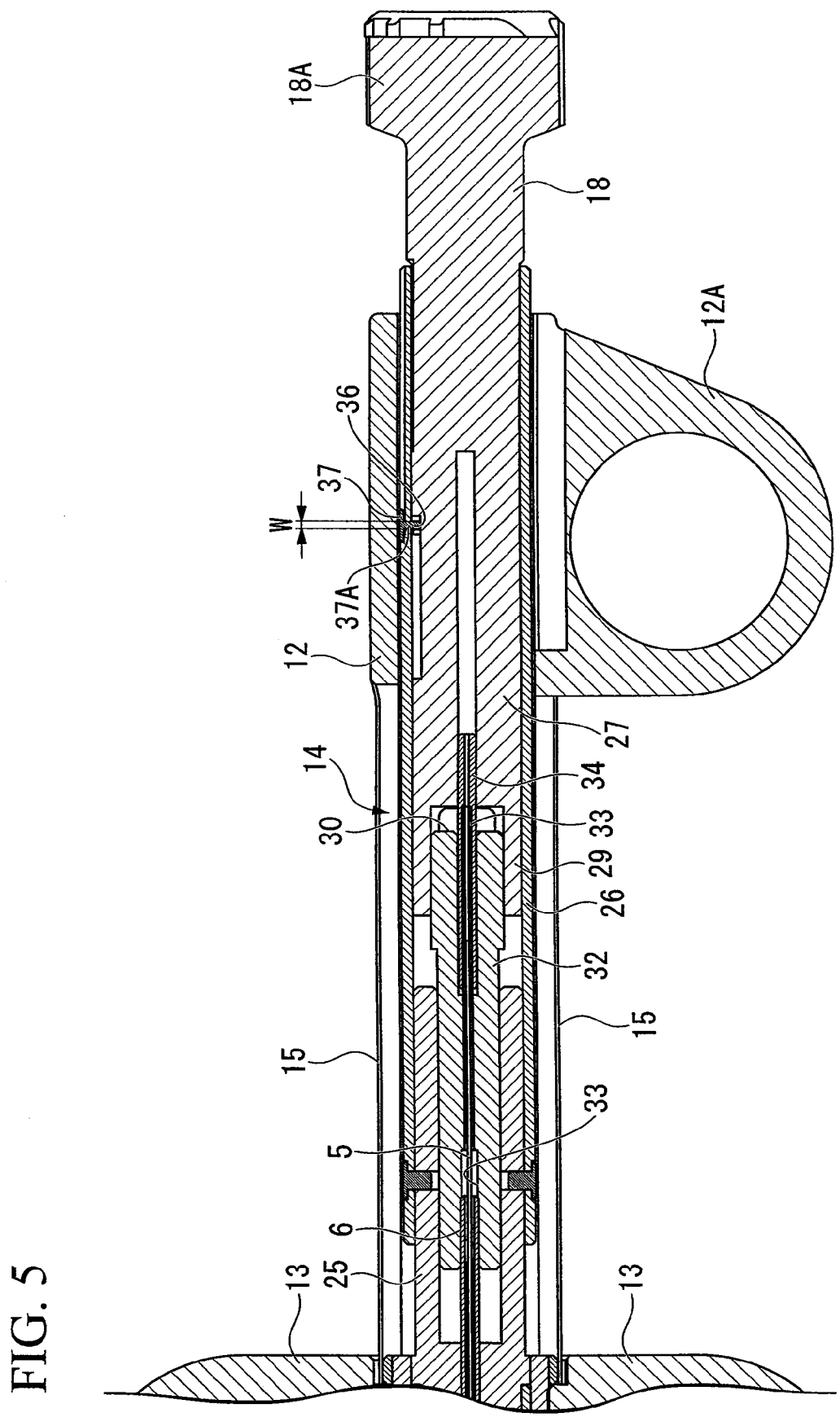
FIG. 5 is an enlarged fragmentary sectional view of the operation section of the suture instrument.

FIGS. 4 and 5 show the operation section 3 in a fragmentary cross-sectional view. The operation section 3 provided proximally relative to the therapeutic insertion section 2 is configured to include: a main operation unit 12 having the proximal end of the outer sheath 8 fixed thereto; a slide section 13 attached to the main operation unit 12 and being capable of sliding in the axial line direction of the main operation unit 12; and a distal end operation section 14 inserted into the main operation unit 12.

The main operation unit 12 formed by a resin or other materials has a substantially cylindrical lateral wall member 15. A proximal end 8A of the outer sheath 8 is fixed to the distal end of the main operation unit 12 by means of, for example, bonding or crimping. A distal end cap 16 formed to be greater than the diameter of the main operation unit 12 and being capable of making contact with the slide section 13 is disposed in the vicinity of the distal end of the main operation unit 12.

The distal end cap 16 is designed to prevent the slide section 13 from moving distally beyond the distal end of the main operation unit 12 and to optimize the position of the slide section 13 contacting the distal end cap 16 in view of the discharge of the needle 4 from the outer sheath 8.

A finger hook ring section 12A formed to bulge outward in the radial direction from a part of the outer periphery of the main operation unit 12 in the circumferential direction is provided on the proximal end of the main operation unit 12.

The slide section 13 has a pair of finger hook ring sections 13A formed to bulge from the outer periphery of the main operation unit 12 in the circumferential direction outwardly in the radial direction. In addition, the slide section 13 has a substantially cylindrical coupling member 25 fixed thereto.

The coupling member 25 is inserted into the main operation unit 12 and has the outer periphery section of an opening formed in the proximal end of the tube 7. In this configuration, the linear movement of the slide section 13 along the axial line of the main operation unit 12 causes the tube 7 to advance or retract relative to the outer sheath 8. The wire 5 and the inner coil sheath 6 project from the opening of the proximal end of the coupling member 25.

The distal end operation section 14 includes a guide mechanism 23 and a rod section 18. In this configuration, the guide mechanism 23 is accommodated in the main operation unit 12 and controls the advancing or retracting movement of the wire 5 and the inner coil sheath 6 connected to the wire 5 which advance from the opening formed on the proximal end of the therapeutic insertion section 2 relative to the main operation unit 12; and the rod section 18 is fixed to the proximal end of the guide mechanism 23 and projects from the opening formed on the proximal end of the main operation unit 12 in the axial direction.

The guide mechanism 23 is configured to include: a cylindrical member 26 having the proximal end section of the coupling member 25 inserted and attached therein; and a substantially cylindrical engagement member 27 inserted into the cylindrical member 26 and fixed to the distal end of the rod section 18.

Figure 6:
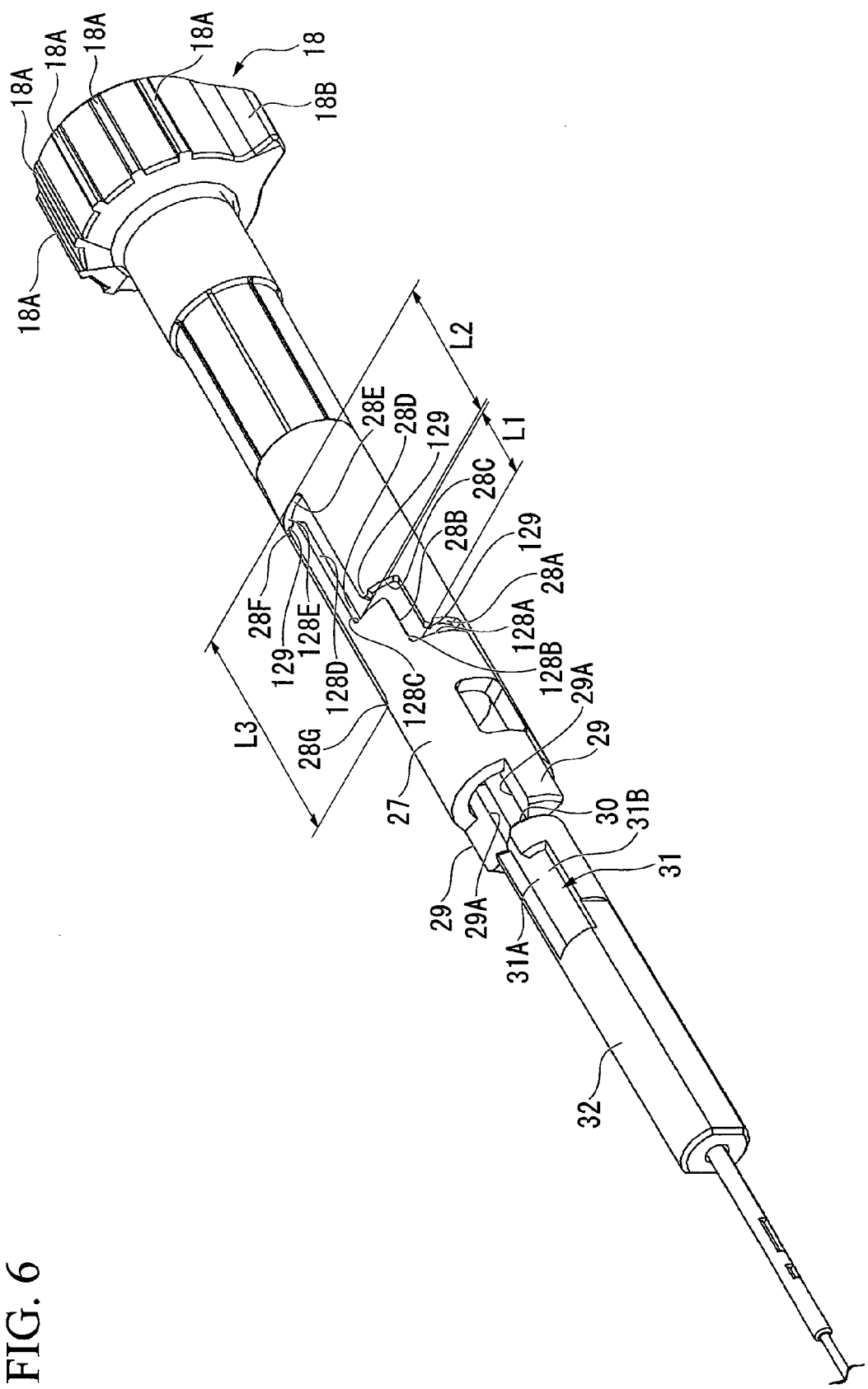
FIG. 6 shows a part of the operation section of the suture instrument.

FIG. 6 shows a part of the inside of the operation section 3. The engagement member 27 has a guide groove 28 advancing in the circumferential direction and the axial direction on the outer periphery. To be more specific, the guide groove 28 is a continuous groove formed by a first lateral groove 128A, a first longitudinal groove 128B, a second lateral groove 128C, a second longitudinal groove 128D, a third lateral groove 128E, and a third longitudinal groove 128F. The first lateral groove 128A advances from a position 28A defined on a part of the outer periphery to a position 28B rotated in a clockwise direction from the position 28A by a predetermined angle $\theta 1$ (in the present embodiment, the predetermined angle $\theta 1$ is 45 degrees. See FIG. 10) around the axial line viewed from the proximal end of the engagement member 27 in the circumferential direction. The first longitudinal groove 128B advances from the position 28B bent from the first lateral groove 128A by 90 degrees toward the proximal end of the engagement member 27 and further advances to the proximal end of the engagement member 27 in the axial line direction by a length L1 to reach a position 28C. The second lateral groove 128C advances from the position 28C to a position 28D, rotated around the axial line in a clockwise direction by the predetermined angle $\theta 1$ viewed from the proximal end of the engagement member 27. The second longitudinal groove 128D advances from the position 28D bent from the second lateral groove 128C by 90 degrees toward the proximal end of the engagement member 27 and further advances to a position 28E which is disposed proximally in the axial line direction of the engagement member 27 by the length L1 or a length L2 which is not shorter than the length L1. The third lateral groove 128E advances from the position 28E to a position 28F rotated in a clockwise direction around the axial line by the predetermined angle $\theta 1$ viewed from the proximal end of the engagement member 27. The third longitudinal groove 128F advances from the position 28F bent from the third lateral groove 128E by 90 degrees toward the distal end of the engagement member 27 and further advances to a position 28G disposed distally in the axial line direction of the engagement member 27 by the sum of length L1 and the length L2 or by a length L3 longer than the sum of L1 and L2.

In addition, the first lateral groove 128A, the second lateral groove 128C and the third lateral groove 128E each has a protrusion section 129 on a part of an inner wall section thereof in which the protrusion section 129 bulges from the inner wall of the guide groove 28 and narrows the width of the guide groove 28.

In addition, a pair of distal engagement sections 29 formed on the distal end section of the engagement member 27 project from two opposed points on the outer periphery of the distal end in the radial direction. The distal engagement sections 29 each have a projection section 29A which projects distally in the axial direction and inwardly in the radial direction. In addition, an abutment surface 30 makes contact with the engagement member 27, and a substantially cylindrical advance-and-retraction movement section 32 has a mating engagement section 31 which engages with the distal engagement section 29. The abutment surface 30 and the advance-and-retraction movement section 32 are placed between the engagement member 27 and the coupling member 25.

The mating engagement section 31 is configured to include recessed sections 31A and recessed fitting sections 31B. The recessed sections 31A are formed at positions each rotated from the abutment surface 30 in a counterclockwise direction around the axial line by the predetermined angle θ1. The distal ends of the distal engagement sections 29 can be inserted into the recessed sections 31A simultaneously. The recessed fitting sections 31B are formed at positions each rotated from the recessed section 31A in a counterclockwise direction around the axial line by another predetermined angle θ1. The projection sections 29A of the distal engagement section 29 fitting into the recessed fitting section 3 1B.

As shown in FIG. 5, the distal end section of the freely advancing and retractable advance-and-retraction movement section 32 is inserted into the coupling member 25, and the outer periphery of the opening formed on the proximal end of the inner coil sheath 6 is inserted and fixed in a through-hole 33 formed along the axial line. In addition, the freely advancing and retractable wire 5 inserted through the inner coil sheath 6 and further inserted and supported by the through-hole 33 projects from the opening formed on the proximal end and is fixed to the engagement member 27 disposed on the proximal end via reinforcement tubes 34 and 35.

In addition, a through-hole 36 formed on the cylindrical member 26 penetrates from the outer periphery to the inner periphery thereof. A pin 37 inserted and fixed in the through-hole 36 is directed from outward in the radial direction to inward in the radial direction. A distal end section 37A of the pin 37 is inserted in the guide groove 28. In addition, the distal end section 37A of the pin 37 is configured to be capable of advancing or retracting along the guide groove 28 while pressing the protrusion section 129 since the pin 37 has a diameter W smaller than the width of the guide groove 28.

In addition, as shown in FIGS. 5 and 6, the rod section 18 is a substantial cylindrical member inserted in the proximal end of the main operation unit 12. The rod section 18 has a plurality of line projection sections 18A each bulging from the proximal end thereof in the radial direction and being formed to be along the axial line; and an indicator section 18B further projecting from a part of the outer periphery of the proximal end thereof in the radial direction. The indicator section 18B is a stopper where a user places their finger and indicates the position of the rod section 18 relative to the main operation unit 12 for the user.

Operations in use of the suture instrument 1 having the aforementioned configuration will be explained as follows with reference to FIGS. 7 to 22.

Figure 7:
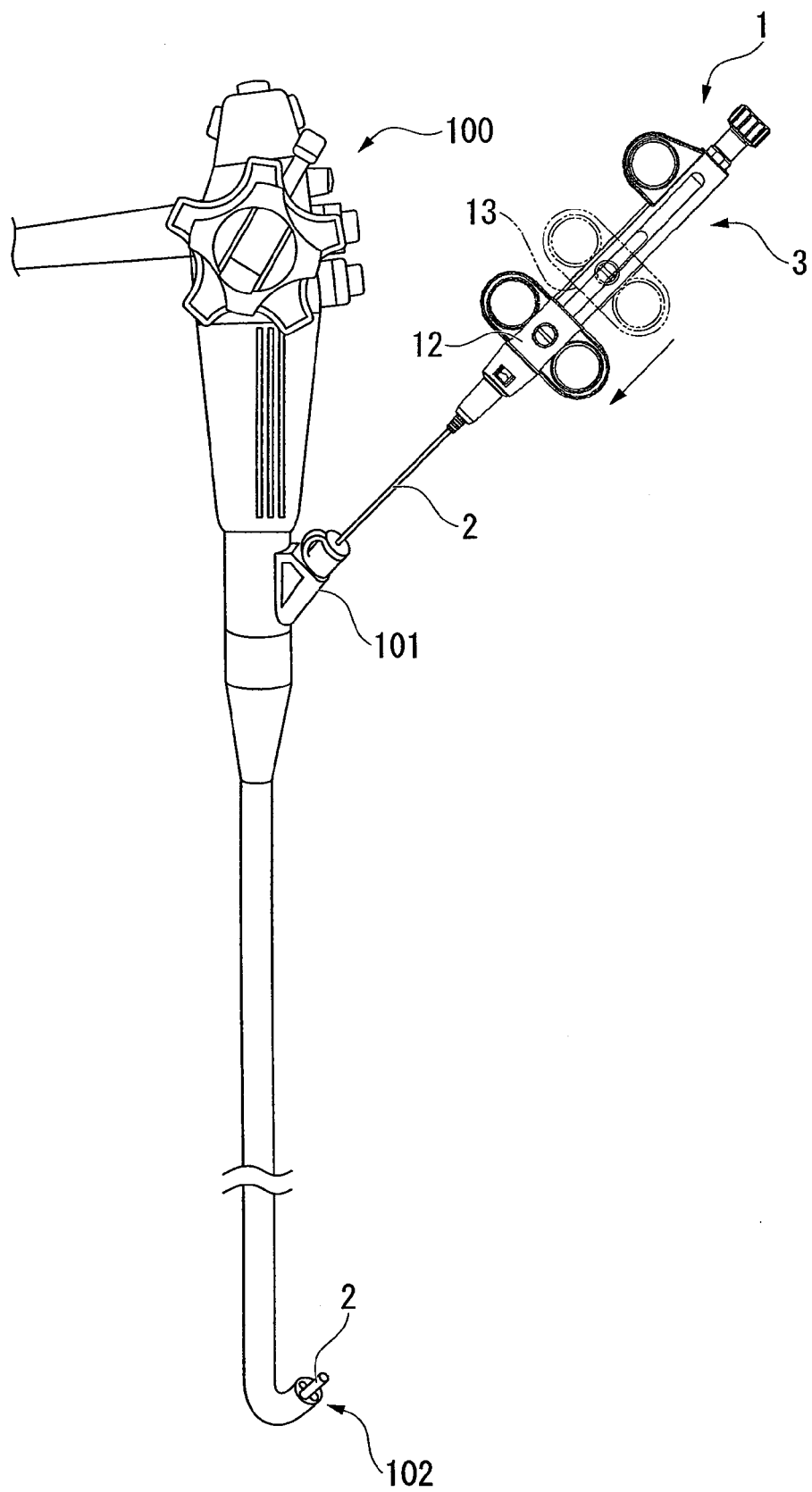
FIG. 7 shows the operation section and a therapeutic insertion section of the suture instrument in use.

To begin with, an endoscope apparatus 100 is inserted into a body of a patient, and the distal end of the endoscope apparatus 100 is approached in the vicinity of a treatment object tissue, such as a hole. As shown in FIG. 7, the distal end of the suture instrument 1 in use inserted into a forceps port 101 of the endoscope apparatus 100 is projected from an operation channel 102 into the body of the patient.

Figure 8:
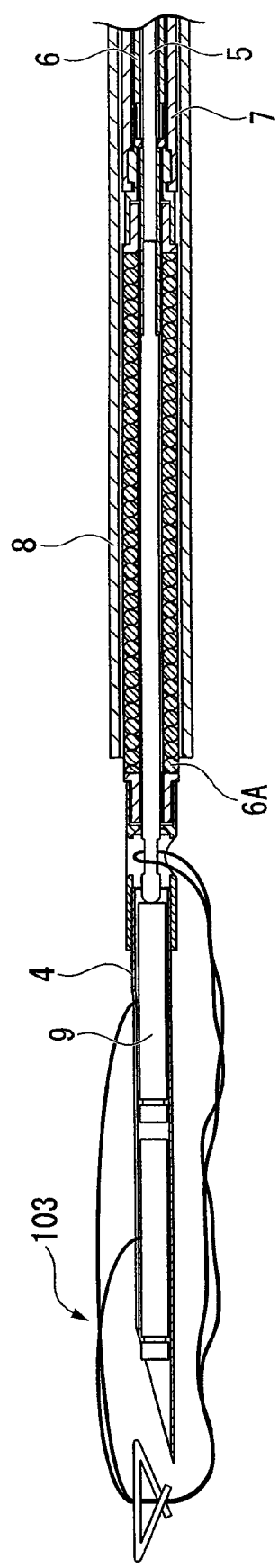
FIG. 8 shows a process of a suturing operation using the suture instrument.

As shown in FIG. 7, the user slides the slide section 13 distally. Subsequently, as shown in FIG. 8, the needle 4 and the suture unit 103 attached to the needle 4 are exposed from the distal end of the outer sheath 8.

It should be noted that the positional correlation between the tube 7 and the needle 4 and the positional correlation between the wire 5 and the inner coil sheath 6 do not vary since the distal end operation section 14 attached to the slide section 13 via the coupling member 25 moves distally when the slide section 13 is slid distally.

Figure 9:
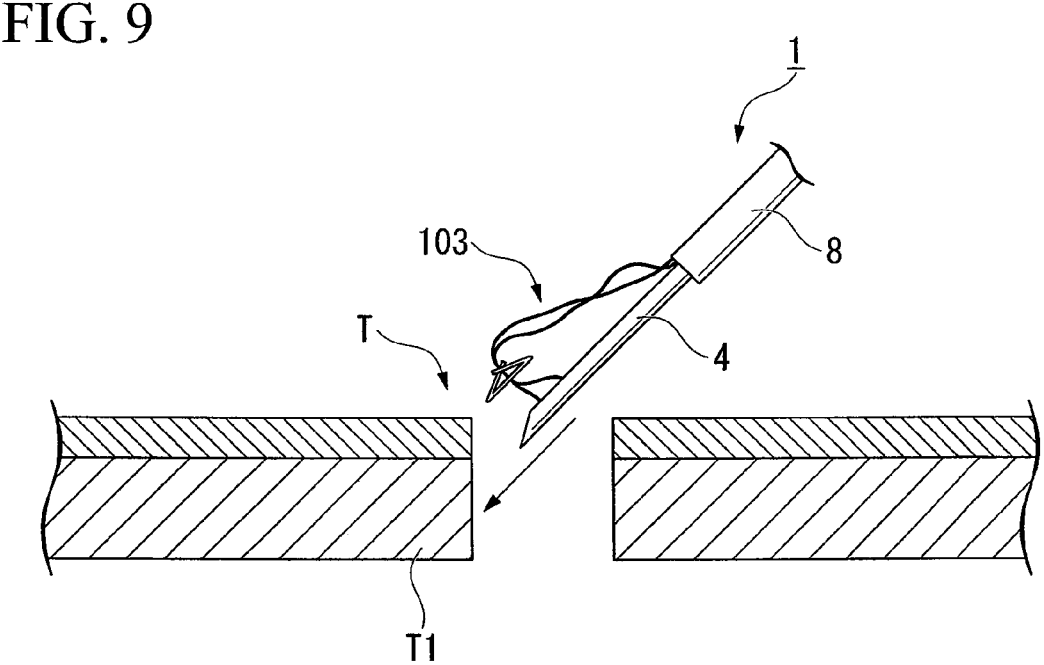
FIG. 9 shows a process of a suturing operation using the suture instrument.

As shown in FIG. 9, the user approaches the distal end of the suture instrument 1 having the needle 4 in a projected state to an object tissue T around, for example, the hole and inserts and penetrates the needle 4 into a tissue T1.

Figure 10:
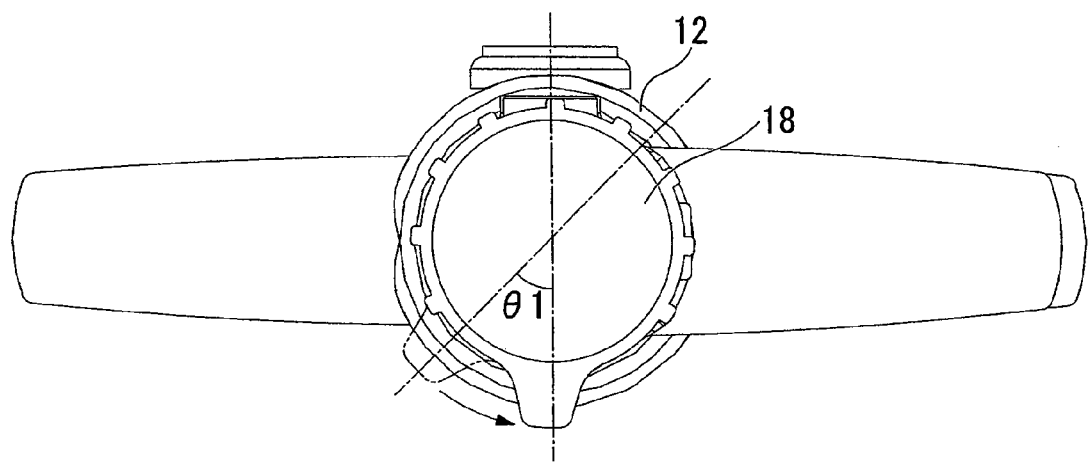
FIG. 10 shows the movement of a rod section of the suture instrument during use thereof.
Figure 11:
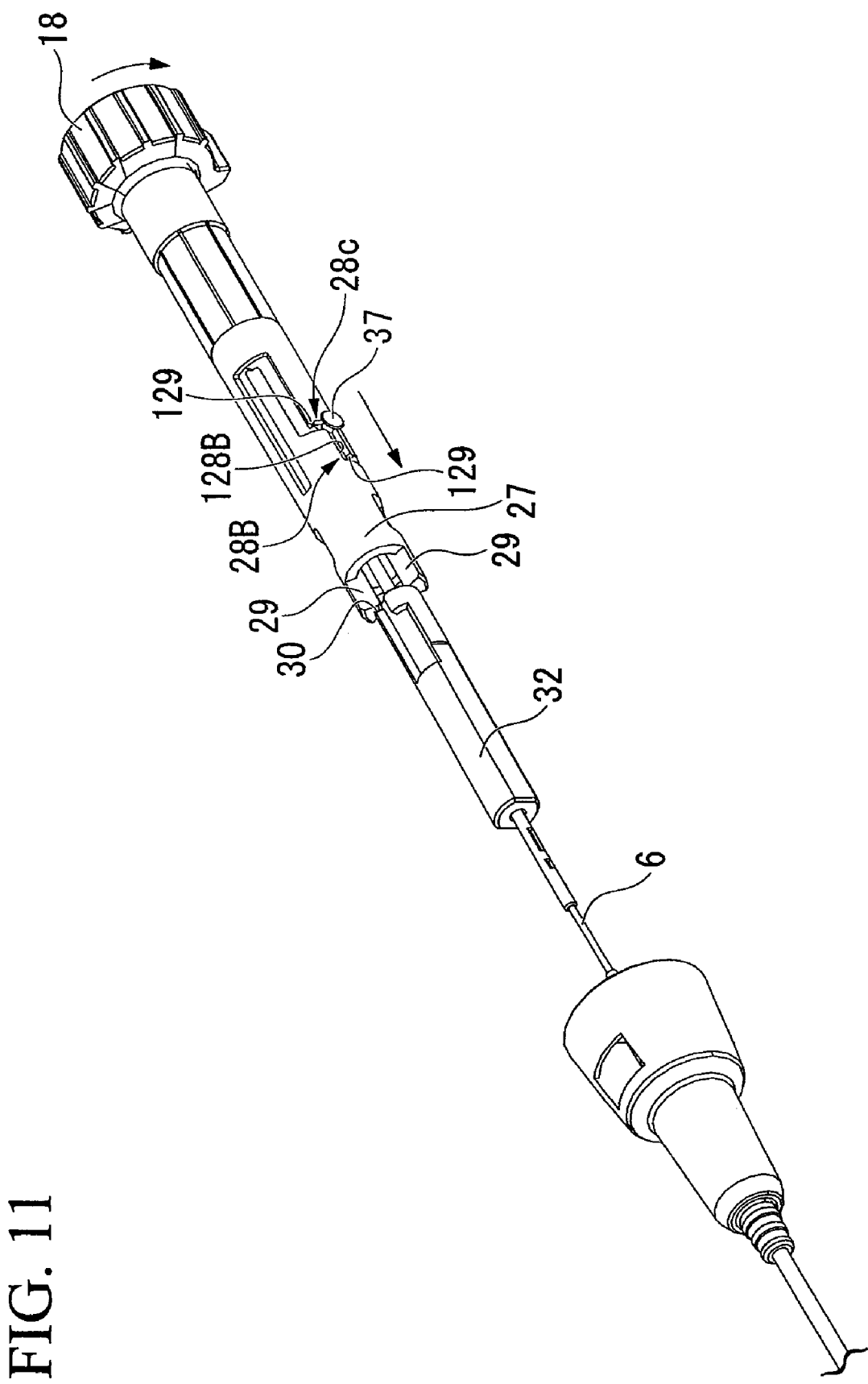
FIG. 11 shows the movement of the operation section of the suture instrument during use thereof.
Figure 12:
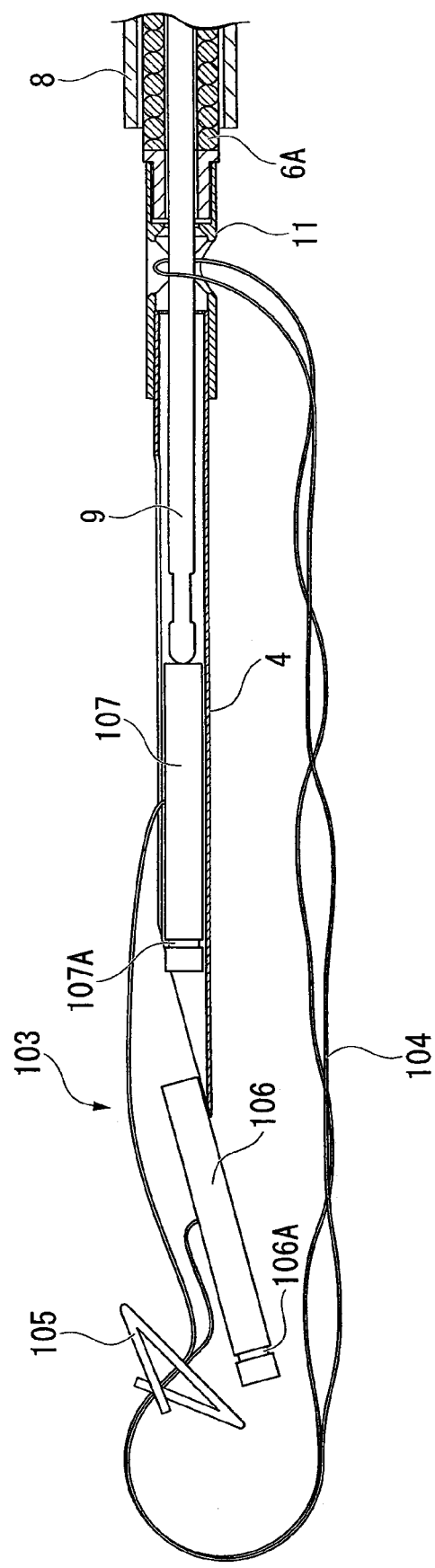
FIG. 12 shows the movement of a distal end section of the suture instrument during use thereof.

As shown in FIGS. 10 and 11, the user upon penetrating the tissue T1 with the needle 4 rotates the rod section 18 in a counterclockwise direction viewed from the proximal end around the axial line relative to the main operation unit 12 by the predetermined angle θ1. Subsequently, the pin 37 moves from the position 28A to the position 28B, and makes contact with the inner wall of the first longitudinal groove 128B; thus a rotation in the circumferential direction stops. This operation causes the engagement member 27 to rotate in a counterclockwise direction by the predetermined angle θ1 relative to the main operation unit 12 and the cylindrical member 26. Resistance produced by this state of the pin 37 pressing and passing by the protrusion section 129 is transferred to the user, and the rotation of the rod section 18 in the counterclockwise direction is limited. Subsequently, the user pushes the rod section 18 into the main operation unit 12. Then, the pin 37 guided by the first longitudinal groove 128B moves to the position 28C. The engagement member 27 in this state moves distally relative to the cylindrical member 26 by the length L1. The distal engagement section 29 of the engagement member 27 making contact with the abutment surface 30 of the advance-and-retraction movement section 32 presses and moves the advance-and-retraction movement section 32 distally. The inner coil sheath 6 is pressed and moved by the length L1 since the proximal end of the inner coil sheath 6 is fixed to the advance-and-retraction movement section 32. The inner coil sheath 6 presses and moves the abutment section 10 provided to the proximal end of the pusher's distal end section 9 at the distal end of the therapeutic insertion section 2. Accordingly, as shown in FIG. 12, the first anchor 106 and the second anchor 107 disposed in the distal end of the pusher's distal end section 9 are pressed and moved by the length L1, and the first anchor 106 is discharged from the distal end of the needle 4. Simultaneously, a engagement groove 107A of the second anchor 107 engages with an engagement protrusion disposed at a position where the first anchor 106 has been previously accommodated.

Figure 13:
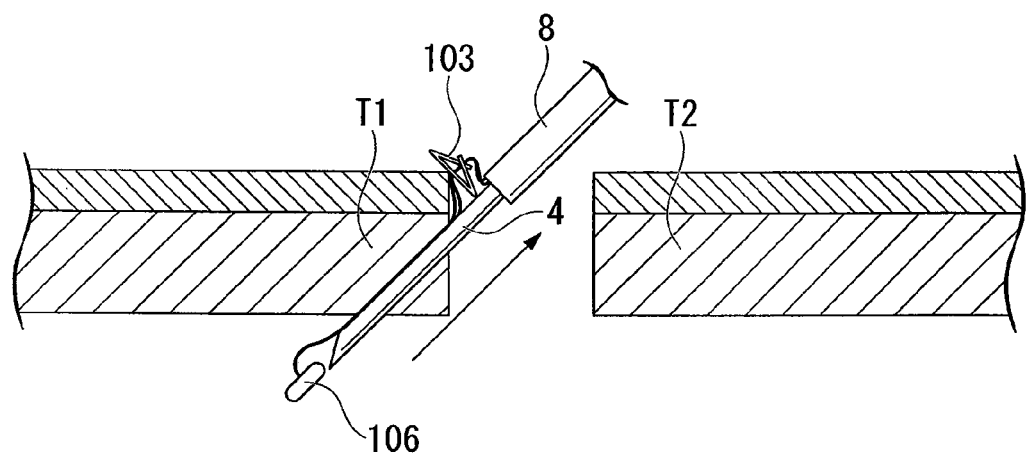
FIG. 13 shows a process of a suturing operation using the suture instrument.

As shown in FIG. 13, the user removes the needle 4 from the tissue T1 having the first anchor 106 in the discharged state. The first anchor 106 in this state locks the tissue T1. Subsequently, the needle 4 is inserted and penetrated into a tissue T2 which is opposed to the tissue T1 with respect, for example, to a hole.

Figure 14:
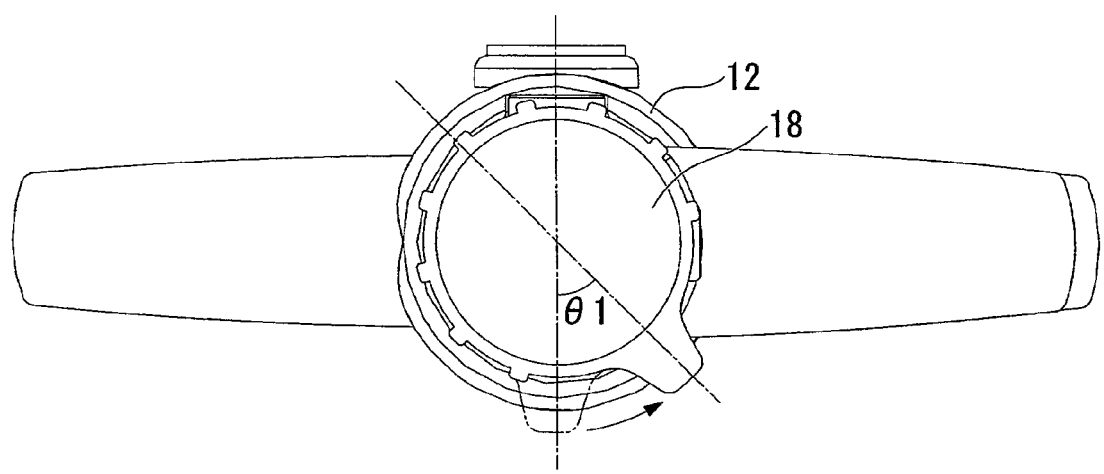
FIG. 14 shows the movement of the rod section of the suture instrument during use thereof.
Figure 15:
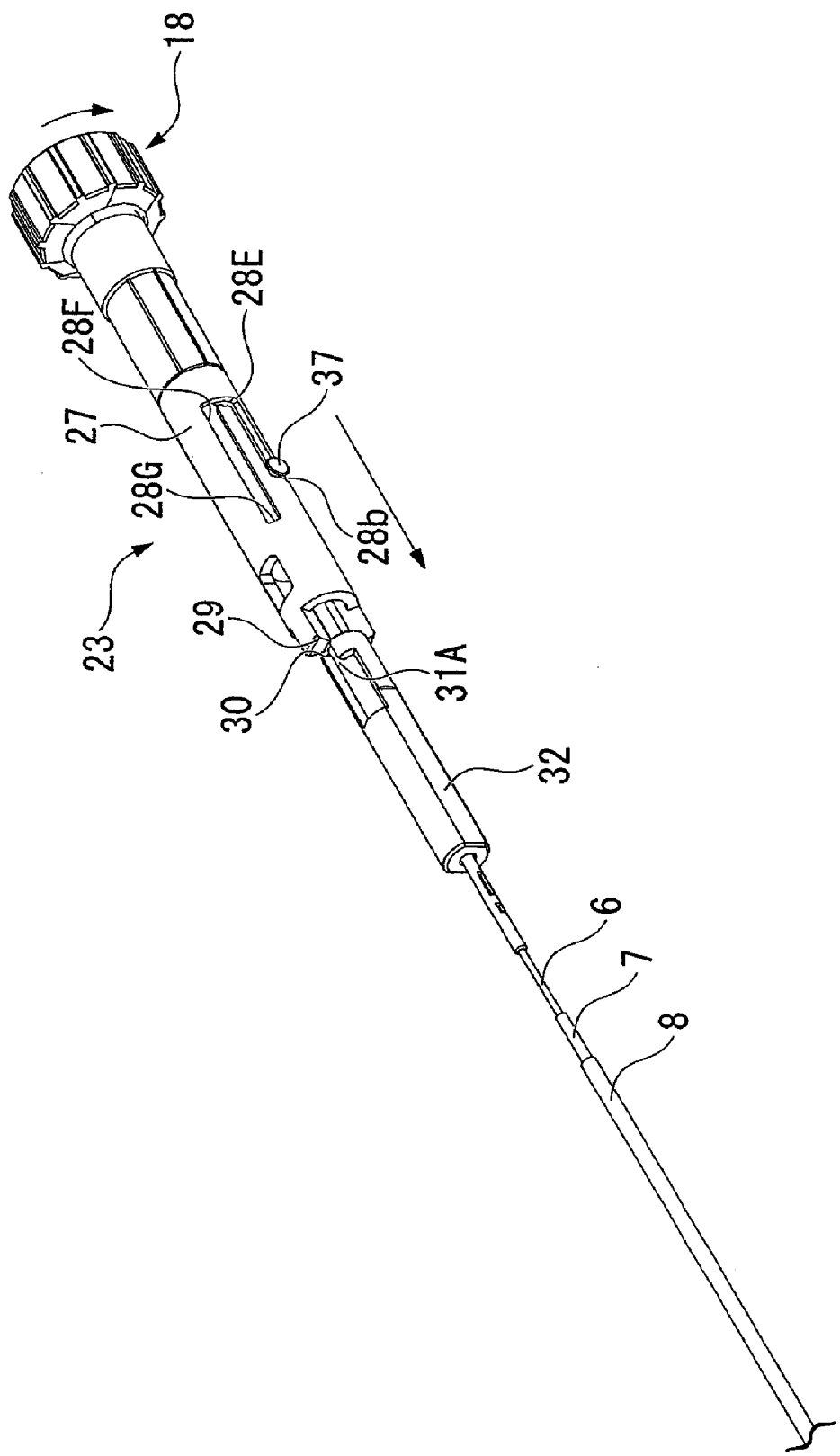
FIG. 15 shows the movement of the operation section of the suture instrument during use thereof.
Figure 16:
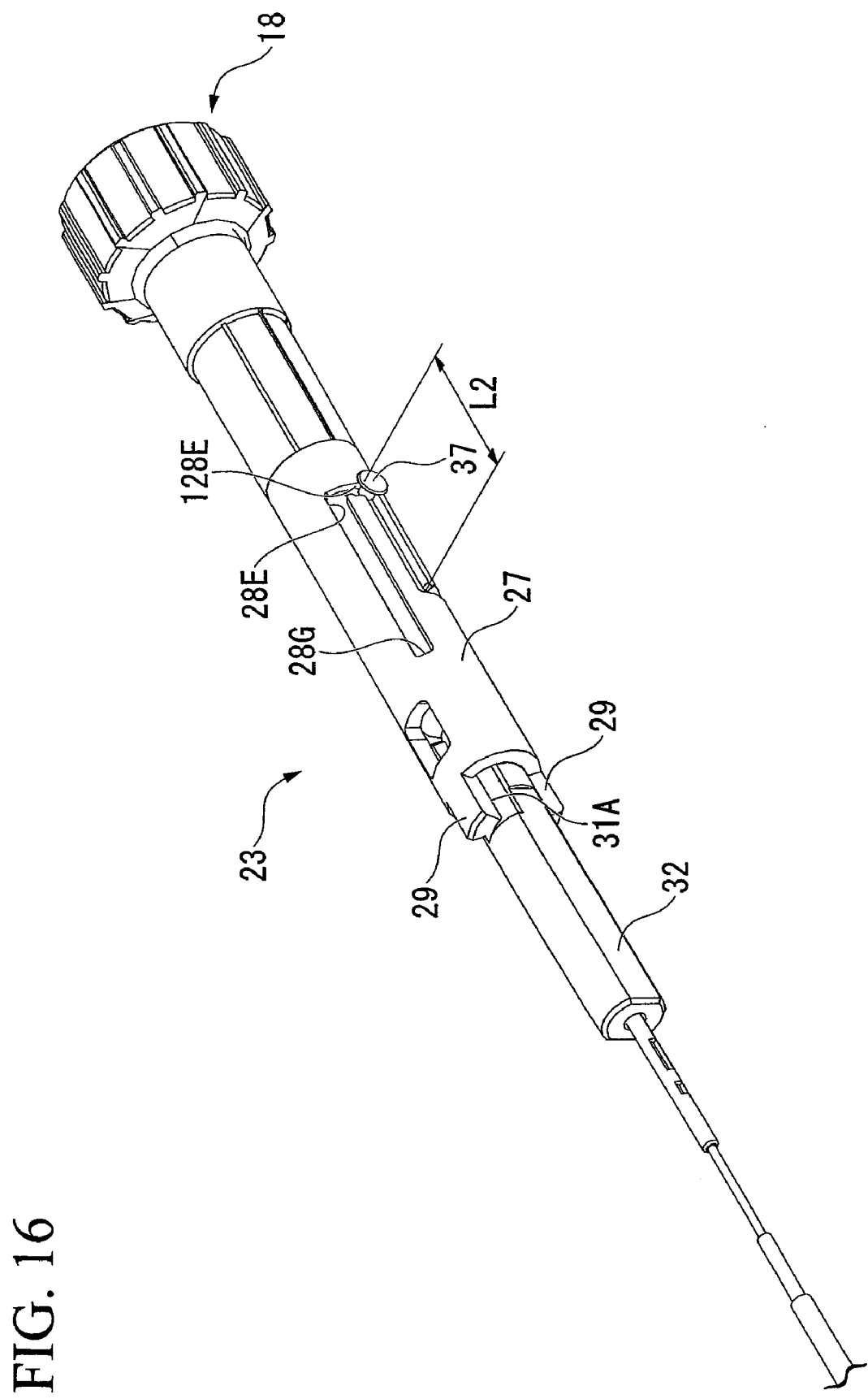
FIG. 16 shows the movement of the operation section of the suture instrument during use thereof.
Figure 17:
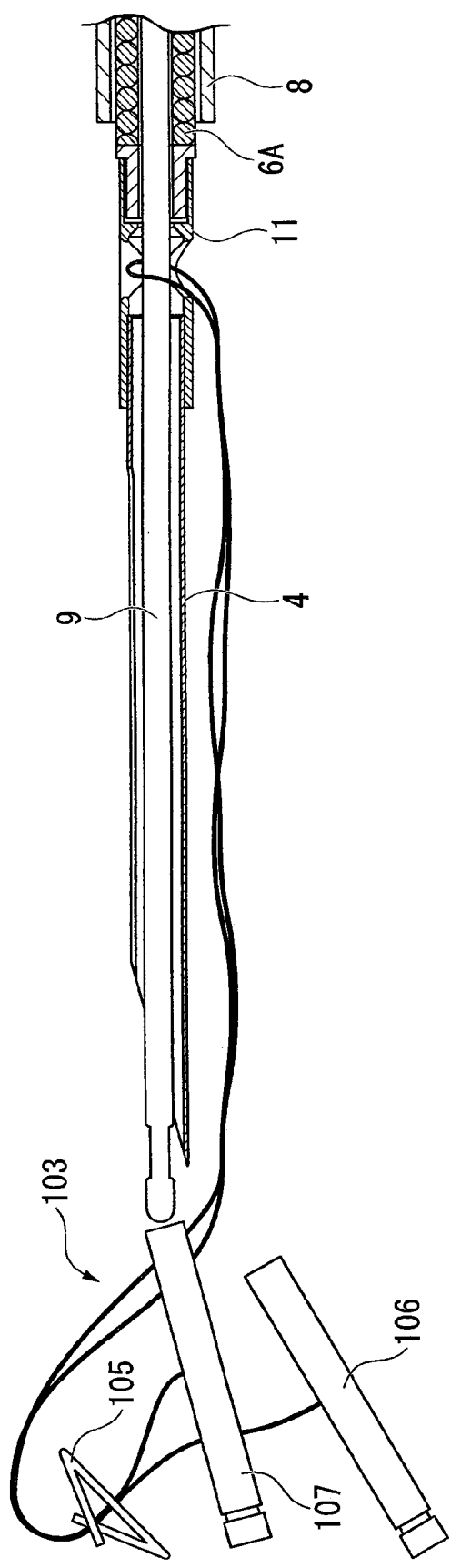
FIG. 17 shows the movement of the distal end section of the suture instrument during use thereof.
Figure 18:
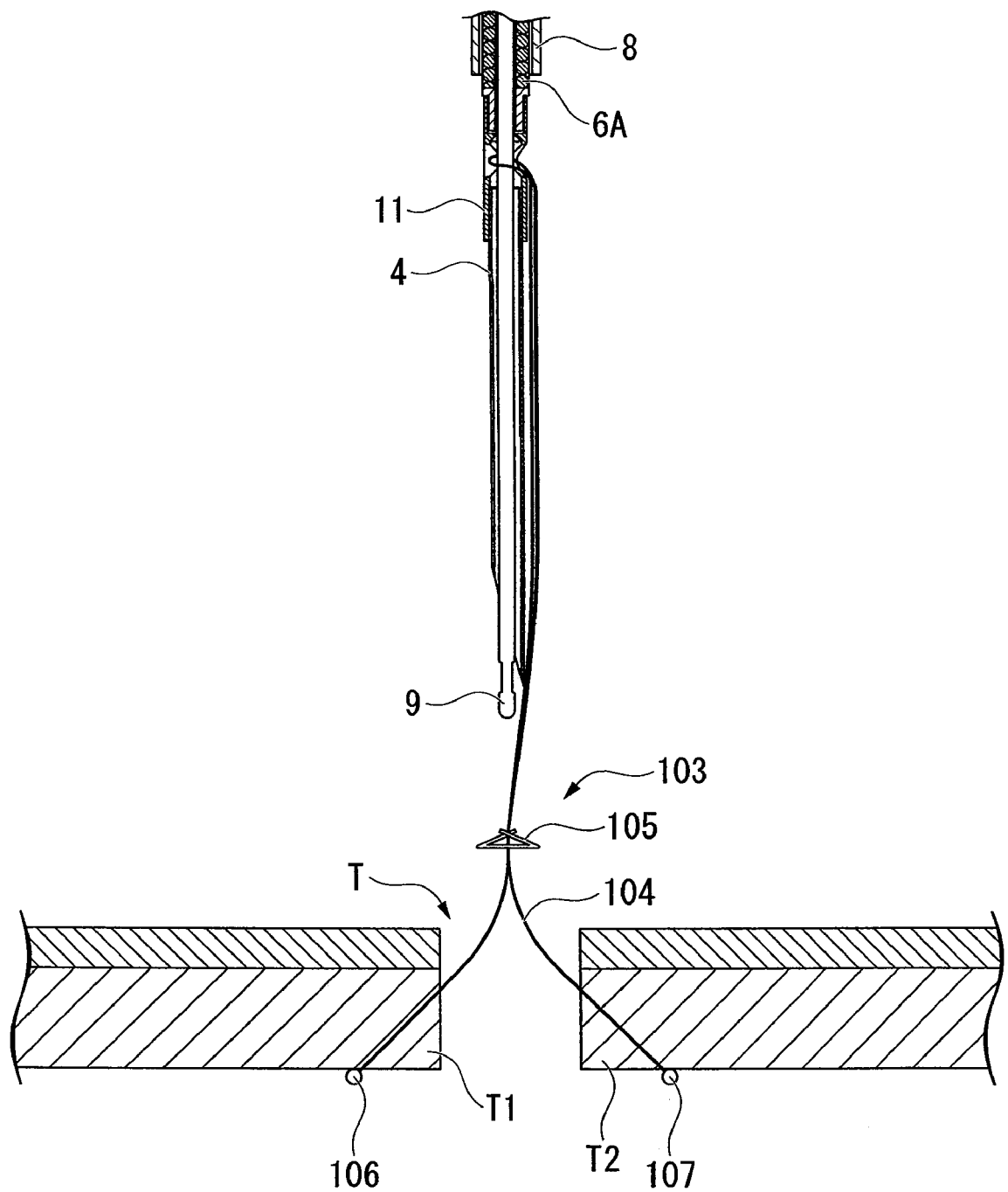
FIG. 18 shows a process of suturing operation using the suture instrument.

As shown in FIG. 14, the user upon penetrating the tissue T2 with the needle 4 further rotates the rod section 18 in a counterclockwise direction. Subsequently, the pin 37 guided by the guide groove 28 moves from the position 28C to the position 28D. The distal engagement section 29 of the distal end section of the engagement member 27 in this state rotates in the circumferential direction around the axial line viewed from the proximal end section by the predetermined angle θ1. The distal engagement section 29 shifts from the abutment surfaces 30 of the advance-and-retraction movement section 32 to the recessed sections 31A of the mating engagement section 31. Subsequently, the user pushes the rod section 18 into the main operation unit 12. Subsequently, as shown in FIG. 16, the engagement member 27 moves distally by the length L2 until the pin 37 makes contact with the inner wall section of the third lateral groove 128E of the guide groove 28, and then, the distal engagement sections 29 are inserted into the recessed sections 31A. The position of the inner coil sheath 6 relative to the tube 7 in the distal end of the therapeutic insertion section 2 does not vary since the advance-and-retraction movement section 32 is not pressed or moved by the advance or retraction of the engagement member 27 in this state. On the other hand, as shown in FIG. 17, the pusher's distal end section 9 is pressed and moved in the distal end of the therapeutic insertion section 2 since the wire 5 is connected to the distal end section of the engagement member 27 via the reinforcement tubes 34 and 35. The distal end of the pusher's distal end section 9 presses the proximal end of the second anchor 107. Consequently, the second anchor 107 is pushed out of the needle 4. As shown in FIG. 18, the user upon discharging the second anchor 107 removes the needle 4 from the tissue T2 and locks the tissue T2 with the second anchor 107.

Figure 19:
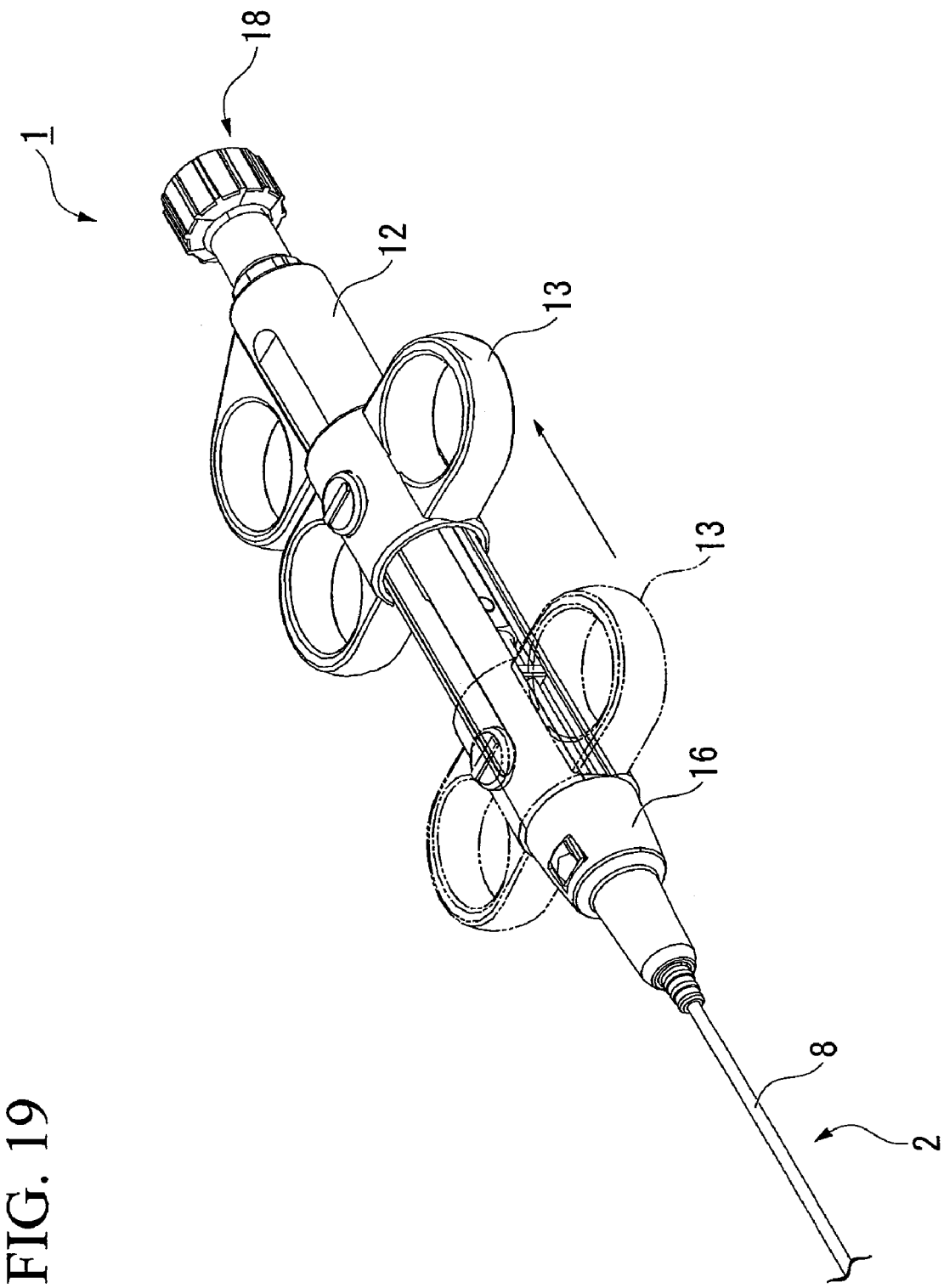
FIG. 19 shows a process of suturing operation using the suture instrument.

As shown in FIG. 19, the user retracts this state of the slide section 13 proximally relative to the main operation unit 12 and accommodates the tube 7 and the needle 4 in the outer sheath 8. Positions of the wire 5 and the pusher's distal end section 9 relative to the needle 4 do not vary since this state of the distal end operation section 14 is retracted together with the slide section 13.

Figure 20:
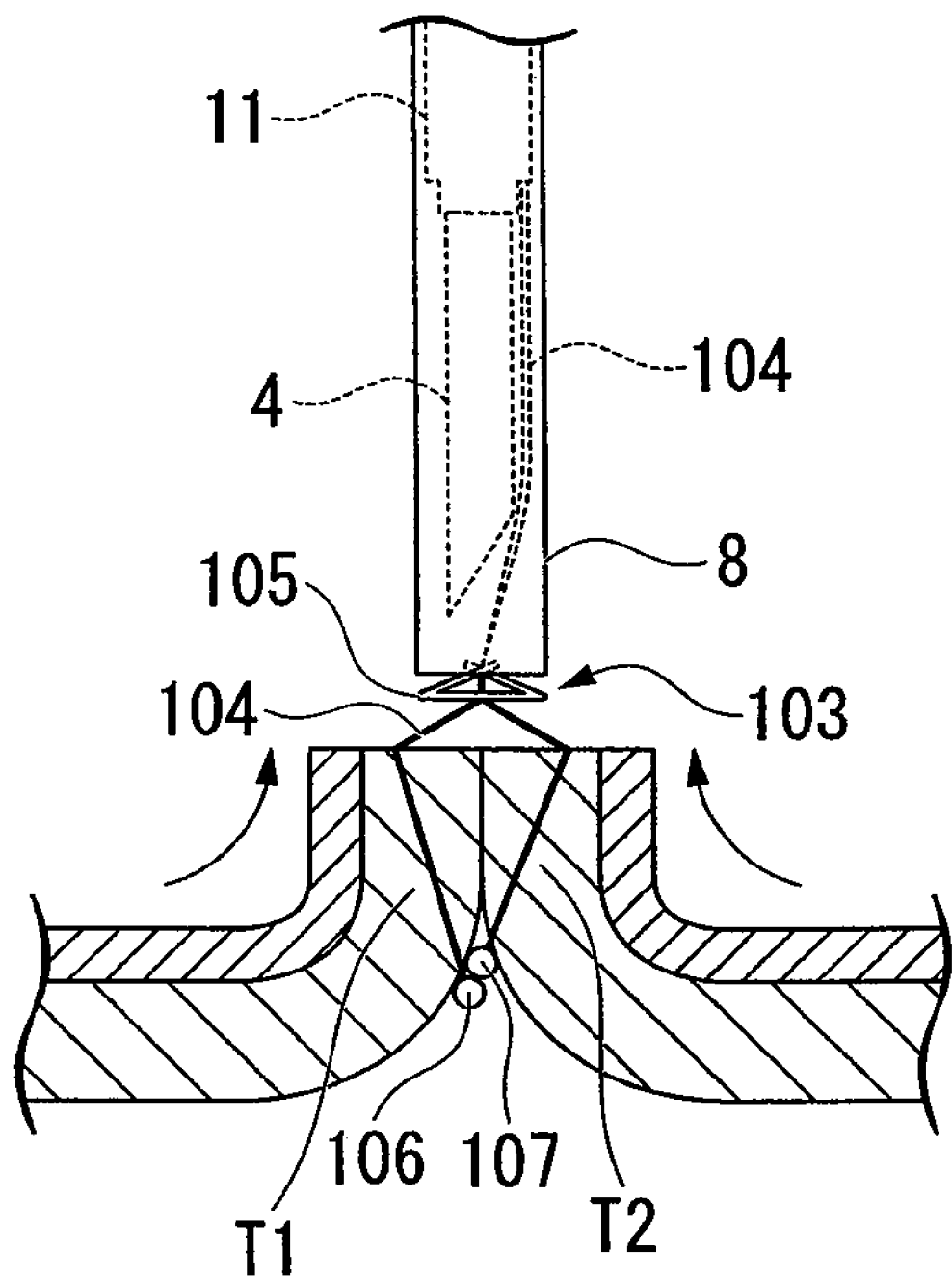
FIG. 20 shows a process of suturing operation using the suture instrument.

Subsequently, as shown in FIG. 20, the suture thread 104 of the suture unit 103 looped around the pusher's distal end section 9 is accommodated in the outer sheath 8; thus, the stopper 105 makes contact with the distal end of the outer sheath 8. Further retraction of the slide section 13 conducted by the user causes the suture thread 104 alone to be accommodated in the inner coil sheath 6 while the stopper 105 makes contact with the inner coil sheath 6, thereby shortening the distance between the stopper 105 and the anchor 106, and the distance between the stopper 105 and the anchor 107.

The tissues T1 and T2 together with the anchors 106 and 107 are attracted to and adhered by the suture instrument 1 while the stopper 105 approaches the anchors 106 and 107 since the anchors 106 and 107 lock the tissues T1 and T2 respectively. The object tissue T is sutured in this manner.

The suture thread 104 in this state can move relative to the stopper 105 since the engagement between the end section 105A and the end section 105B of the stopper 105 is loose when accommodating the suture thread 104 into the outer sheath 8. In contrast, the movement in the aforementioned direction in an attempt to move the suture thread 104 toward the anchors 106 and 107 is impossible since the end section 105A engages with the end section 105B more strongly by a force acting on the suture thread 104. That is, the sutured state of the object tissue T is free from slack or disengagement since the stopper 105 is capable of moving toward the anchors 106 and 107 and incapable of the reverse movement.

Figure 21:
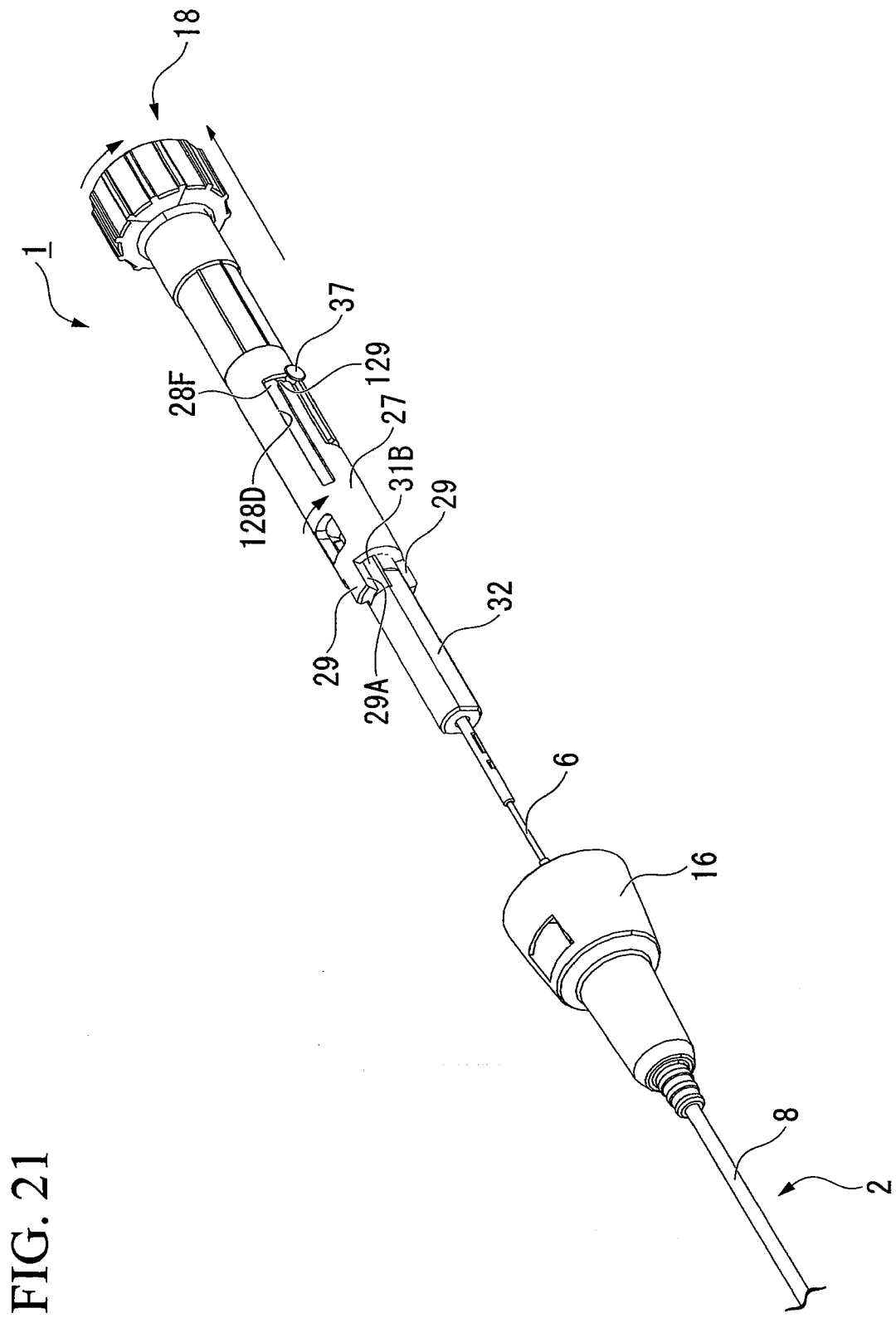
FIG. 21 shows the movement of the operation section of the suture instrument during use thereof.

As shown in FIG. 21, the user upon finishing the suture further rotates the rod section 18 in a counterclockwise direction viewed from the proximal end around the axial line by the predetermined angle θ1. Subsequently, the pin 37 moving from the position 28E to the position 28F of the guide groove 28 and making contact with the inner wall section of the third longitudinal groove 128F at the position 28F provides a positional correlation in which the engagement member 27 is rotated relative to the cylindrical member 26 by another predetermined angle θ1. In addition, the distal engagement sections 29 of the distal end of the engagement member 27 in this state rotate by the predetermined angle θ1, and each projection section 29A of the distal engagement section 29 fits into each recessed fitting section 31B adjacent to each recessed sections 31A. The user removes this state of the rod section 18 proximally relative to the main operation unit 12. Subsequently, the force for removing the rod section 18 proximally transferred to the recessed fitting section 31B via the projection section 29A and to the wire 5 and the pusher's distal end section 9 fixed to the engagement member 27 causes the wire 5, the pusher's distal end section 9, and the inner coil sheath 6 to be removed proximally and simultaneously.

Figure 22:
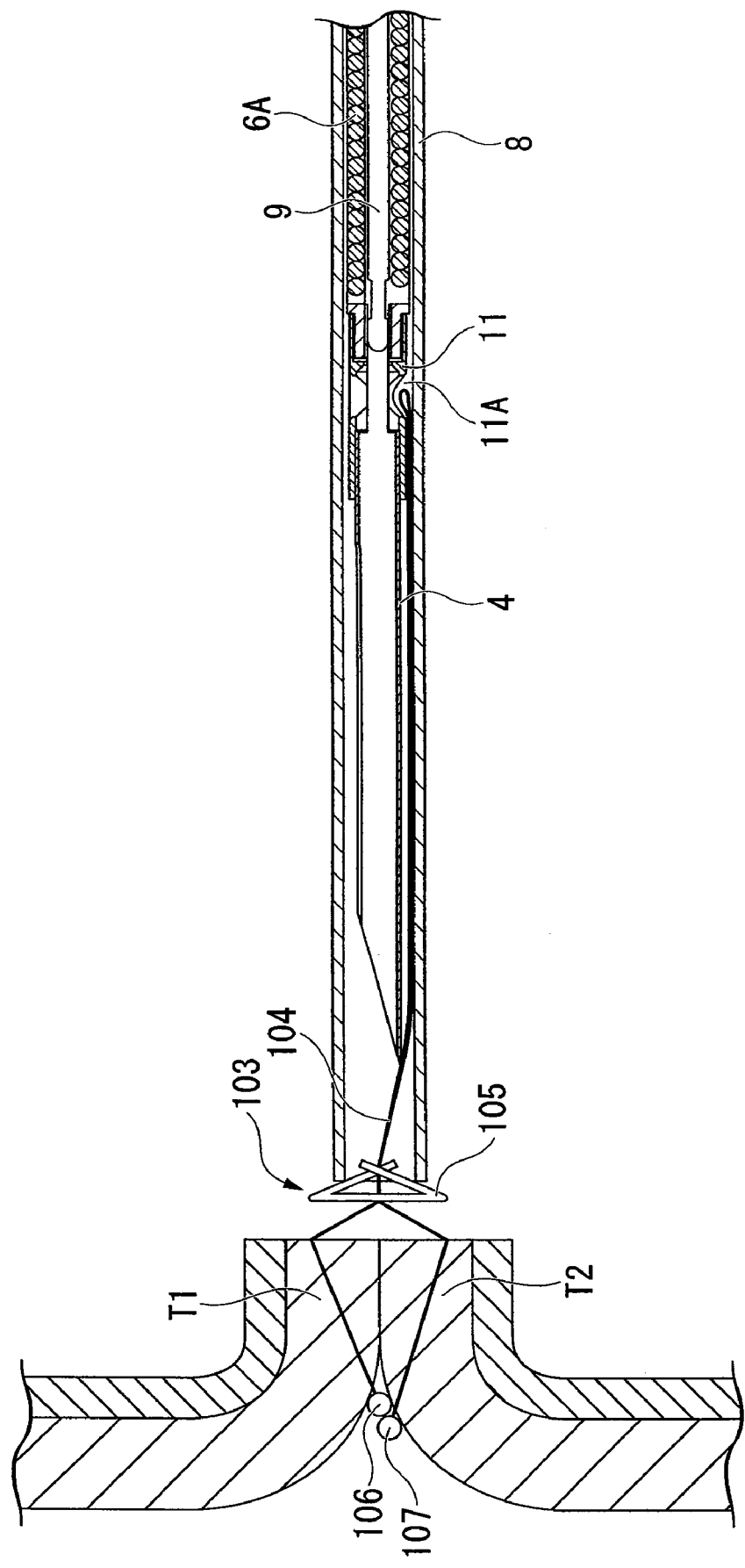
FIG. 22 shows a process of a suturing operation using the suture instrument.

As shown in FIG. 22, moving the distal end of the pusher's distal end section 9 proximally relative to the connection tube 11 causes the suture thread 104 to be removed from the pusher's distal end section 9, thereby detaching the suture unit 103 from the suture instrument 1. A sequence of treatment concludes in this manner.

In an attempt to avoid a concurrent discharge of anchors, an example of conventional suture instruments discharges anchors one after another. However, a mechanism of this type had problems to be solved which include a case in which a plurality of anchors are discharged concurrently when a strong force is applied to press the pusher's distal end section, or a case in which complex operation causes erroneous movement since a user must change a holding position of an operation section if a specific mechanism is provided to discharge a second anchor.

The suture instrument 1 according to the present embodiment enables an operation of discharging the first anchor 106 from the needle 4 by holding the main operation unit 12 and pushing the slide section 13 in the axial direction while enabling an operation of discharging the second anchor 107 after discharging the first anchor 106 by similarly holding the main operation unit 12 and pushing the slide section 13 in the axial direction. In addition, anchors can be discharged one after another reliably by conducting an operation of rotating the rod section 18 in the circumferential direction between the operation of discharging the first anchor 106 and the operation of discharging the second anchor 107; therefore, the user is free from a position change in holding the main operation unit 12 and the rod section 18. Accordingly, erroneous operations can be reduced since a simple operation of repeating a rotational movement of the rod section 18 in the circumferential direction and a linear movement of the rod section 18 in the axial direction alternately can conclude a suturing treatment.

In addition, it is possible to prevent an unsuccessful detachment of the suture thread 104 from the pusher's distal end section 9 which is caused by a step section which attracts the suture thread 104 proximally when the wire 5 is removed proximally since the distal end section of the pusher's distal end section 9 is longer than the distance between the distal end of the needle 4 and the through-hole 11A, and since the suture thread 104 is free from contact with the step section having the abutment section 10 formed thereon.

A second embodiment of the present invention will be explained next with reference to FIG. 23. A suture instrument 41 according to the present embodiment is different from the aforementioned suture instrument 1 because a guide mechanism uses a rotative cam mechanism 42 in place of the guide mechanism 23 according to the first embodiment.

It should be noted that configurations that are similar to those of the previously explained first embodiment will be assigned the same numeric symbol and redundant explanations thereof will be omitted.

Figure 23:
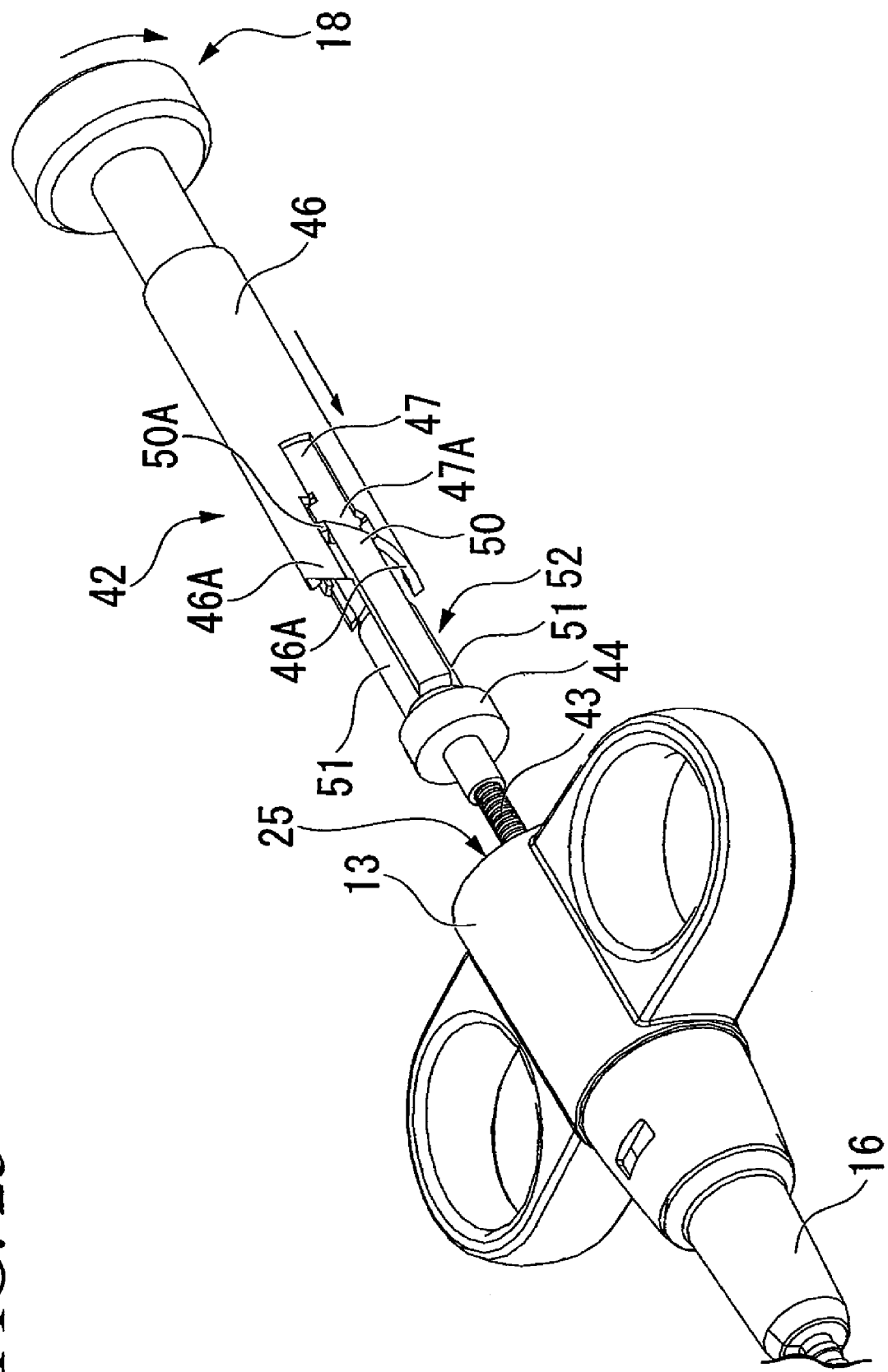
FIG. 23 shows a part of the configuration of a suture instrument according to a second embodiment of the present invention.

FIG. 23 shows a part of the configuration of the suture instrument 41 in enlarged view. The suture instrument 41 includes the rotative cam mechanism 42 in place of the guide mechanism 23 according to the first embodiment. In this configuration, the proximal end section of the inner coil sheath 6 and the proximal end section of the inner coil sheath 6 are connected to the distal end section of the rotative cam mechanism 42 respectively; and the rod section 18 is fixed on the proximal end section.

The rotative cam mechanism 42 is configured to include a coil spring 43, a substantially cylindrical support member 44, an advance-and-retraction movement section 52, a cylindrical member 46, and an engagement member 47. The coil spring 43 is fixed to the slide section 13 via the coupling member 25 and has the inner coil sheath 6 passing through the coil spring 43. The support member 44 is fixed to the proximal end of the coil spring 43 and has the inner coil sheath 6 inserted through the support member 44. The advance-and-retraction movement section 52 is coupled to the support member 44 and is freely rotatable in the circumferential direction relative to the support member 44. An opening end section provided on the proximal end of the inner coil sheath 6 makes contact with the advance-and-retraction movement section 52. The wire 5 projecting from the opening end section provided on the proximal end of the inner coil sheath 6 passes through the advance-and-retraction movement section 52. The cylindrical member 46 is disposed coaxially to the proximal end in the axial line direction of the advance-and-retraction movement section 52 and locked to the main operation unit 12. The engagement member 47 inserted into the cylindrical member 46 is freely advancing and retractable and makes contact with the end section of the proximal end of the advance-and-retraction movement section 52. The rod section 18 is fixed to the proximal end of the engagement member 47.

The cylindrical member 46 has a plurality of oblique cam sections 46A. Each oblique cam section 46A projects toward the distal end in the axial direction along the circumferential direction in an outer edge section of the distal end, and has an oblique and spiral surface shape of the projecting end around the axial line. In addition, the cylindrical member 46 has a lock mechanism, not shown in the drawing, on a part of the outer surface in the circumferential direction for locking the cylindrical member 46 to the main operation unit 12 detachably. In addition, a recessed engagement section, not shown in the drawing, which is subject to a fitting contact with the advance-and-retraction movement section 52, is formed on the lateral wall section of the proximal end of the oblique cam section 46A.

The engagement member 47 capable of freely advancing or retractable is inserted in the cylindrical member 46. A plurality of projecting oblique cam sections 47A in the same shape and size are formed on the distal end section of the engagement member 47 in the circumferential direction at predetermined intervals. The surface shape of each projecting end of the oblique cam section 47A is the same as the spiral and oblique surface shape of the oblique cam section 46A.

An oblique cam section 50 advancing proximally in the axial direction is formed on the advance-and-retraction movement section 52. The oblique cam section 50 makes contact with the oblique cam section 46A and the oblique cam section 47A in the vicinity of the distal end of the cylindrical member 46 and the distal end of the engagement member 47.

In addition, mating engagement sections 51 which engage with the oblique cam section 46A are formed on two end sections of the oblique cam section 50 in the circumferential direction viewed from the proximal end of the advance-and-retraction movement section 52. In addition, a projection section 50A projecting in the circumferential direction and making a fitting engagement with the recessed fitting section of the cylindrical member 46 is formed on the lateral wall section of the proximal end of the oblique cam section 50.

Operations in use of the suture instrument 41 having the aforementioned configuration will be explained with reference to FIG. 23.

The user penetrates the tissue TI with the needle 4 in the same fashion as the first embodiment. Subsequently, the rod section 18 is pushed into the main operation unit 12. Subsequently, the engagement member 47 fixed to the rod section 18 moves distally relative to the main operation unit 12, and the oblique cam section 47A of the distal end of the engagement member 47 making contact with the oblique cam section 50 inserted between the oblique cam sections 46A is pressed and moved distally in the axial line direction while being guided by opposed wall sections of the oblique cam sections 46A. It should be noted that, since the oblique cam section 50 is biased proximally by the coil spring 43, a pression force in the circumferential clockwise direction viewed from the proximal end is produced and acts on the oblique cam section 50 pressed by the oblique cam section 47A; therefore, the oblique cam section 46A presses the oblique cam section 50.

The inner coil sheath 6 moving distally relative to the tube 7 causes the first anchor 106 to be discharged similarly to the first embodiment since the distal end of the advance-and-retraction movement section 52 in this state is connected to the inner coil sheath 6.

The oblique cam section 50 rotates and moves around the axial line along the oblique section of the oblique cam section 47A to a oblique cam 46B (not illustrated in FIG. 23 since this component is disposed on the back side of the suture unit) and is locked there since the support to the oblique cam section 50 by the lateral wall sections of the oblique cam sections 46A is released when the oblique cam section 50 is pressed to move beyond the distal ends of the oblique cam sections 46A. A tactile response produced by rotating this state of advance-and-retraction movement section 52 and transferred to the user allow the user to acknowledge that the first anchor 106 is ready for discharge. Subsequently, the user penetrates the tissue T2 with the needle 4 in the same fashion as in the first embodiment.

The user pushes the rod section 18 into the main operation unit 12 once again while the needle 4 is penetrated into the tissue T2. Subsequently, the engagement member 47 is inserted from the proximal end into the mating engagement section 51 of the advance-and-retraction movement section 52. The wire 5 disposed along the axial line in the vicinity of the distal end of the engagement member 47 is pressed and moved by the engagement member 47 while the advance-and-retraction movement section 52 in this state makes no advancing or retracting movement in the axial line direction. This results in causing the wire 5 to move distally relative to the advance-and-retraction movement section 52. Subsequently, the wire 5 pressing and moving the pusher's distal end section 9 causes the second anchor 107 to be discharged in the same fashion as the first embodiment. Subsequently, the rod section 18 pushed by the user into the main operation unit 12 causes the engagement member 47 to move farther distally. Subsequently, the oblique cam section 47A of the engagement member 47 presses and moves the oblique cam section 50 of the advance-and-retraction movement section 52. The advance-and-retraction movement section 52 upon releasing the engagement between the oblique cam section 50 and the oblique cam section 47A makes rotational movement around the axial line. The projection section 50A in this state fitting into the recessed fitting section 46D (not illustrated in FIG. 23 since this component is disposed on the back side of the suture unit) causes the cylindrical member 46 to be connected to the advance-and-retraction movement section 52, thereby providing synchronous advance and retraction.

Subsequently, the user attracts the slide section 13 proximally relative to the main operation unit 12 in the same fashion as the first embodiment and sutures the object tissue T by retracting the needle 4 into the outer sheath 8. In addition, the user draws the cylindrical member 46 together with the advance-and-retraction movement section 52 by retracting the rod section 18 proximally relative to the main operation unit 12 and removes the inner coil sheath 6 and the wire 5 proximally relative to the needle 4. This results in causing the pusher's distal end section 9 to be retracted proximally relative to the needle 4 and causing the distal end of the wire 5 to move proximally relative to the connection tube 11, thereby disengaging the suture thread 104 from the wire 5 and separating the suture unit 103 from the suture instrument 1 in the same fashion as in the first embodiment. A sequence of treatment concludes in this manner.

The suture instrument 41 according to the present embodiment prevents an erroneous movement of discharging a plurality of anchors in an operation since the pression provided to move the needle 4 distally by the pusher's distal end section 9 is configured to be separate into a pression for moving the advance-and-retraction movement section 52 and a pression for moving the proximal end section of the wire 5. In addition, the configuration adopting the rotative cam mechanism 42 resolves a complex operation conducted in a sequence of discharging a plurality of anchors since the user upon discharging the first anchor 106 by simply pushing the rod section 18 readily acknowledges that the second anchor 107comes to the position ready for discharge.

Although the present invention has been described with respect to its preferred embodiments, the present invention is not limited to the embodiments described above. The configuration of the present invention allows for addition, omission, substitution and further modification without departing from the spirit and scope of the present invention.

For example, the aforementioned embodiments are each explained with reference to an example in which an anchor discharged upon penetrating a tissue with a needle is locked to the tissue may be replaced by a configuration in which the anchor is discharged into the tissue from the distal end of a needle halted in the tissue to lock the anchor to a tissue surrounding thereof.

In addition, the present invention is not limited to an example of suturing using two anchors, i.e., the first anchor 106 and the second anchor 107. Each aforementioned embodiment may adopt a configuration having additional guide grooves 28 or rotative cam mechanisms 42 for discharging three or more anchors one after another.

In addition to the aforementioned embodiments adopting the suture unit 103 having the configuration in which the first anchor 106 is connected to the second anchor 107 by the suture thread 104, a configuration in which suture threads each having an anchor connected to an end thereof and engaging with the stopper 105 can achieve the same effect as that of the aforementioned embodiments.

The present invention is not limited to the above descriptions but is limited only by the appended claims.

What is claimed is:

1. A suture instrument comprising:
   therapeutic insertion section comprising a suture section formed on a distal end thereof and the suture section configured to suture a tissue endoscopically;
   a cylindrical main operation unit connected to a proximal end of the therapeutic insertion section;
   a rod section inserted into the main operation unit along an axial line of the main operation unit from a proximal end of the main operation unit;
   a pusher's distal end section for pressing a suture thread and end section members to move, the end section members being connected to at least an end of the suture thread;
   a guide mechanism comprising a cylindrical member disposed to the proximal end of the therapeutic insertion section and connected to a suture section via a connection member; and an engagement member fixed to a distal end of the rod section and inserted into the cylindrical member;
   a distal engagement section projecting distally in an axial direction and inward in the radial direction from an outer periphery of a distal end of the engagement member;
   an advance-and-retraction movement section comprising an abutment section and a mating engagement section, the advance-and-retraction movement section being positioned and configured to advance freely from and to retract freely into the cylindrical member, the abutment section making contact with a distal end of the distal engagement section, and the mating engagement section engaging with the distal engagement section when the rod section is rotated relative to the cylindrical member in the circumferential direction;
   a first pressing member pressing the pusher's distal end section to move corresponding to the operations conducted by the rod section; and
   a second pressing member pressing the pusher's distal end section to move independently from the first pressing member corresponding to a movement of the advance-and-retraction movement section,
   wherein the second pressing member presses the pusher's distal end section to move when the distal end of the distal engagement section makes contact with the abutment section, and
   the first pressing member presses the pusher's distal end section to move when the distal engagement section engages with the mating engagement section.

2. The suture instrument according to claim 1, wherein the guide mechanism further comprises a rotative cam mechanism for rotating the rod section in one way in the circumferential direction by a predetermined interval by pressing the rod section to move distally and for halting the rod section.

3. The suture instrument according to claim 1, wherein the guide mechanism comprises:
   a guide groove comprising:
   a plurality of longitudinal grooves formed on a side of one of the cylindrical member and the engagement member in the circumferential direction extending in an axial line direction, each one of the plurality of longitudinal grooves being disposed at a different angle around the axial line and being capable of guiding the pusher's distal end section along the axial line while being capable of freely advancing and retracting; and
   a plurality of lateral grooves being formed to connect end sections of the plurality of longitudinal grooves with each other in the circumferential direction, the lateral grooves limiting an advancing movement or a retracting movement of the pusher's distal end section; and a projection section fixed to the other one of the cylindrical member and the engagement member and engaging with the guide groove, wherein at least one of the longitudinal grooves provided in the guide mechanism is formed on a position where the distal engagement section engages with the mating engagement section in the circumferential direction.

4. The suture instrument according to claims 1 or 3, wherein the therapeutic insertion section comprises:

a wire thinner than an outer diameter of the pusher's distal end section, one end of the wire being connected to a proximal end of the pusher's distal end section and the other end of the wire making contact with a distal end of the engagement member;

a cylindrical needle comprising a proximal end section and a sharp distal end section, the proximal end section having a through-hole on an outer periphery in the circumferential direction, the needle having a distal end of the pusher's distal end section inserted therethrough; and a flexible tube connected to a proximal end section of the needle and to the guide mechanism respectively, the flexible tube having the wire inserted therethrough, wherein the wire configures the first pressing member.

5. The suture instrument according to claim 4, wherein the tube has a distal end coil sheath made of a flexible material formed on a distal end section of the tube.

6. The suture instrument according to claim 5, wherein the second pressing member comprises an inner coil sheath disposed between the tube and the wire along an axial line of the wire, the inner coil sheath having a proximal end and a distal end, the proximal end of the inner coil sheath being fixed to the advance-and-retraction movement section, the distal end of the inner coil sheath making contact with a surface perpendicular to an axis line generated at a connecting part formed between the distal end of the pusher's distal end section and the wire thinner than the pusher's distal end section, and the inner coil sheath configured to press to move the pusher's distal end section.

7. The suture instrument according to claim 4, wherein the mating engagement section comprises a recessed fitting section halting a movement of the distal engagement section toward a proximal end side when the distal engagement section is engaging thereon;

the engagement member comprises a first pressing member retaining device to move the first pressing member toward proximal end side corresponding to a movement of the engagement member toward a proximal side; and the suture thread is looped around the pusher's distal end section via the through-hole, and the pusher's distal end section has a fixed outer diameter in a range where the suture thread is looped.

8. The suture instrument according to claim 3, wherein a protrusion section provided in the guide groove limits a movement of the projection section along the guide groove.

* * * * *